US012778474B1

(12) United States Patent
Peacock

(10) Patent No.: US 12,778,474 B1
(45) Date of Patent: Nov. 3, 2026

(54) PLR-CORRECTED COGNITIVE LOAD DETECTION FOR XR

(71) Applicant: Snap Inc., Santa Monica, CA (US)

(72) Inventor: Candace Elise Peacock, Boulder, CO (US)

(73) Assignee: SNAP INC., Santa Monica, CA (US)

( * ) Notice: Subject to any disclaimer, the term of this patent is extended or adjusted under 35 U.S.C. 154(b) by 53 days.

(21) Appl. No.: 18/960,710

(22) Filed: Nov. 26, 2024

Related U.S. Application Data

(60) Provisional application No. 63/603,437, filed on Nov. 28, 2023.

(51) Int. Cl.

| | |
|---|---|
| ***A61B 5/16*** | (2006.01) |
| ***A61B 3/11*** | (2006.01) |
| ***G06F 3/01*** | (2006.01) |
| ***G06T 19/00*** | (2011.01) |

(52) U.S. Cl.
CPC .............. *A61B 5/165* (2013.01); *A61B 3/112* (2013.01); *G06F 3/013* (2013.01); *G06T 19/006* (2013.01)

(58) Field of Classification Search
CPC ......... A61B 5/165; A61B 3/112; G06F 3/013; G06T 19/006
USPC ........................................................ 463/36
See application file for complete search history.

(56) References Cited

U.S. PATENT DOCUMENTS

| | | | | |
|---|---|---|---|---|
| 6,090,051 | A | 7/2000 | Marshall | |
| 10,209,773 | B2 * | 2/2019 | Khaderi | A61B 3/0091 |
| 10,620,700 | B2 * | 4/2020 | Publicover | G02B 27/0093 |
| 10,810,773 | B2 * | 10/2020 | Yildiz | G02B 27/0172 |
| 11,640,572 | B2 | 5/2023 | Zakariaie et al. | |
| 11,666,258 | B2 * | 6/2023 | Shojaeizadeh | A61B 5/163 351/209 |
| 12,367,609 | B2 * | 7/2025 | Noda | G02B 27/0172 |
| 2022/0218198 | A1 | 7/2022 | Devani | |

OTHER PUBLICATIONS

Chen, Fang, et al., "Robust Multimodal Cognitive Load Measurement", Human Computer Interaction Series, (2016), 253 pgs.

(Continued)

*Primary Examiner* — Allen Chan
(74) *Attorney, Agent, or Firm* — SCHWEGMAN LUNDBERG & WOESSNER, P.A.

(57) ABSTRACT

A system, method, and medium for inferring cognitive load of a user of an extended reality (XR) display system. Visual content is presented to a user's eye from a display device. Visual content luminance data is generated, representative of a luminance of the visual content as presented. Environmental light data is generated, representative of environmental light propagating toward the user's eye. Pupil size data representative of a pupil size of the user's eye, and gaze vector data representative of a direction of a gaze vector of the user's eye, are generated. The gaze vector data, visual content luminance data, and environmental light data are processed to generate local luminance data representative of a local luminance at a fixation target of the gaze vector, and global luminance data. The pupil size data, local luminance data, and global luminance data are processed to generate cognitive load data.

20 Claims, 18 Drawing Sheets

(56) References Cited

OTHER PUBLICATIONS

Duchowski, Andrew T., et al., "The Index of Pupillary Activity Measuring Cognitive Load vis a vis Task Difficulty with Pupil Oscillation", Proceedings of the 2018 CHI Conference on Human Factors in Computing Systems, (Apr. 2018), 13 pgs.
Duchowski, Andrew T., et al., "The Low High Index of Pupillary Activity", Association of Computing Machinery, (Apr. 2020), 12 pgs.
Epps, Julien, "Automatic Pupillary Light Reflex Detection in Eyewear Computing", IEEE Transactions on Cognitive and Developmental Systems, (Nov. 2018), 15 pgs.
Mallick, Rohit, et al., "The Use of Eye Metrics To Index Cognitive Workload in Video Games", IEEE Second Workshop on Eye Tracking and Visualization, (Oct. 23, 2016), 6 pgs.
Marshall, Sandra P., "The Index of Cognitive Activity Measuring Cognitive Workload", IEEE 7th Human Factors Meeting, (2002), 5 pgs.
Palinko, Oskar, et al., "Exploring the Influence of Light and Cognitive Load on Pupil Diameter in Driving Simulator Studies", Driving Assessment Conference, (Jan. 2011), 8 pgs.
Raiturkar, Pallavi, et al., "Decoupling Light Reflex from Pupillary Dilation to Measure Emotional Arousal in Videos", Proceedings of the ACM Symposium on Applied Perception, (Jul. 2016), 8 pgs.
Vogels, Jorrig, et al., "The Index of Cognitive Activity as a Measure of Cognitive Processing Load in Dual Task Settings", Frontiers In Psychology vol. 9, (Nov. 2018), 19 pgs.
Walter, Kerri, et al., "Cognitive Load Influences Oculomotor Behavior In Natural Scenes", Scientific Reports, (Jun. 11, 2021), 12 pgs.

* cited by examiner

PLR-CORRECTED COGNITIVE LOAD DETECTION FOR XR

CLAIM OF PRIORITY

This application claims the benefit of priority to U.S. Provisional Application Ser. No. 63/603,437, filed on Nov. 28, 2023, which is incorporated herein by reference in its entirety.

TECHNICAL FIELD

The present disclosure relates generally to display devices and more particularly to display devices and systems used for extended reality.

BACKGROUND

A head-worn device may be implemented with a transparent or semi-transparent display through which a user of the head-worn device can view the surrounding environment. Such devices enable a user to see through the transparent or semi-transparent display to view the surrounding environment, and to also see objects or other content (e.g., virtual objects such as 3D renderings, images, video, text, and so forth) that are generated for display to appear as a part of, and/or overlaid upon, the surrounding environment (referred to collectively as “virtual content”). This is typically referred to as “extended reality” or “XR”, and it encompasses techniques such as augmented reality (AR), virtual reality (VR), and mixed reality (MR). Each of these technologies combines aspects of the physical world with virtual content presented to a user.

Cognitive load defines the cognitive state in which a user’s working memory capacity is exceeded. When this happens, a user may experience fatigue, frustration, and a decrease in task accuracy. XR can induce cognitive load as rendered content is overlaid on the real world and may overload a user’s cognitive system. As XR becomes more integrated into users’ lives, therefore, it can be beneficial for XR systems to infer and reduce cognitive load. This, in turn, can reduce costly errors and increase user satisfaction. However, because cognitive load is an implicit cognitive state, the XR system must infer a user’s cognitive load using behavioral or brain signals since users will not be providing explicit, subjective reports of cognitive load. One way that the system can infer a user’s cognitive load is via eye tracking. In fact, it has been demonstrated that during scene viewing, longer fixation durations are indicative of cognitive load and that, across a range of tasks, increases in pupil size are predictive of cognitive load.

Although both eye movements and pupil size are predictive of cognitive load, the literature suggests that pupil size may be more generalizable across tasks than eye movements. For example, during cognitive load tasks that require speed, fixation durations will become shorter whereas cognitive load tasks that don’t require speed result in increases in fixation duration. Conversely, pupil size increases as cognitive load increases across a range of tasks, suggesting it is a generalizable feature of cognitive load. This may be important in the context of XR, where users could be doing any task at any time, which makes it imperative that the eye tracking features used to predict cognitive load can generalize across tasks.

Although the pupil provides a general signal of cognitive load, it is also sensitive to changes in luminance due to the pupillary light reflex (PLR), making it unreliable in real-world XR settings where luminance can change on a moment to moment basis. The pupil diameter can also be influenced by certain drugs (including some prescription medication and some drugs of abuse), further compounding measurement of cognitive load.

BRIEF DESCRIPTION OF THE SEVERAL VIEWS OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some non-limiting examples are illustrated in the figures of the accompanying drawings in which.

DETAILED DESCRIPTION

Figure 1:
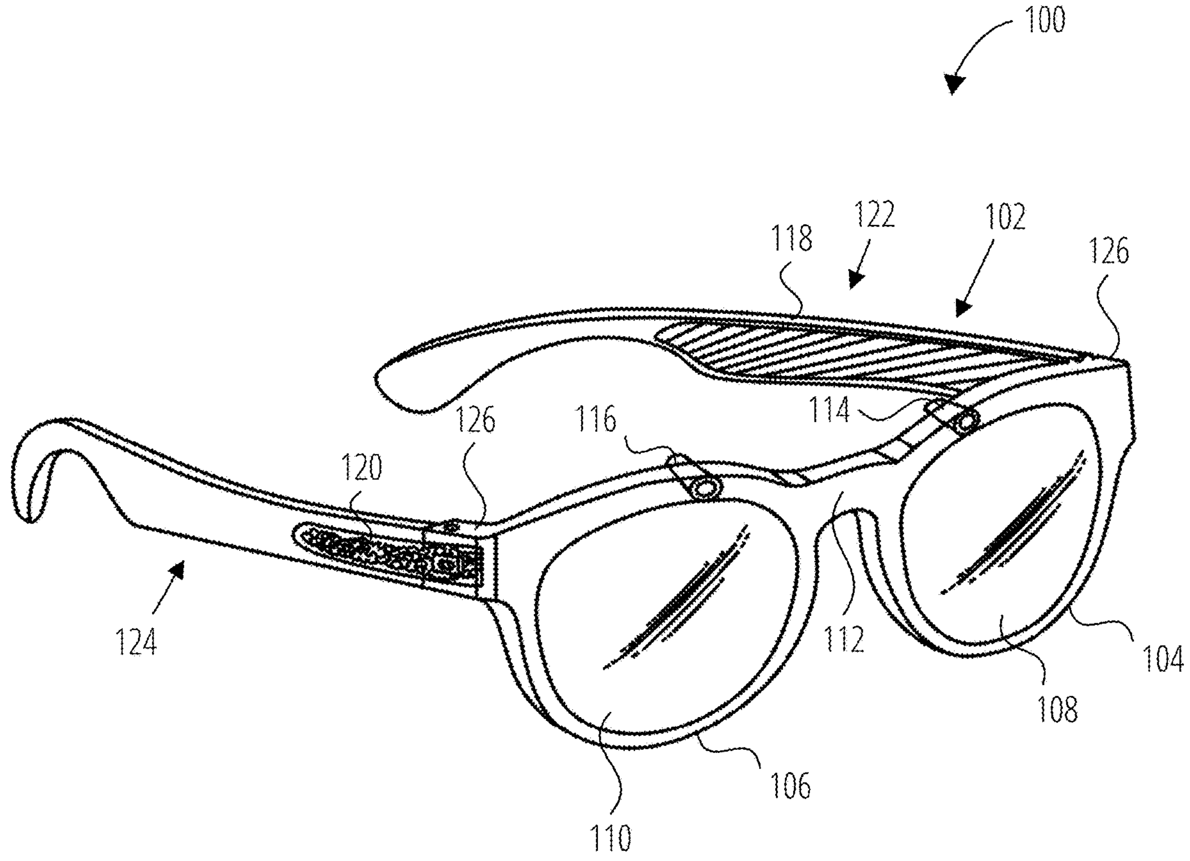
FIG. 1 is a perspective view of a head-worn device, in accordance with some examples.

XR displays are typically categorized as virtual reality displays, video pass-through displays, or optical see-through displays. In virtual reality displays, a virtual environment is presented to the user's eyes, and the real-world physical environment is obscured. In video pass-through, a view of the physical environment is captured by a camera, combined with virtual content, and then presented to the user on an opaque display. In optical see-through, a user views the physical environment directly through transparent or translucent displays which interpose virtual content between the user's eyes and the physical environment. Thus, whereas virtual reality and video pass-through XR systems typically present only projected light to a user's eyes, optical see-through XR systems present both ambient light (from the physical environment) and projected light to the user's eyes. In each case, the light presented to a user's eyes can give rise to the pupillary light reflex (PLR), complicating the task of assessing a user's cognitive load based on pupil size. This problem may be particularly acute in the case of optical see-through displays, because both projected light and ambient light can affect the pupillary light reflex.

There is prior work that attempts to remove the influence of the pupillary light reflex to enable robust cognitive load detection based on tracking changes in pupil size. While this prior work demonstrates that it is possible to remove or control for the pupillary light reflex, these prior attempts exhibit several limitations. In some attempts, controlled environments are used, thereby limiting the generalizability of the techniques to noisy, real-world environments where luminance and cognitive load constantly fluctuate. Some attempts have been made to use features that are purportedly luminance-free, such as oscillatory pupil activity and Haar-like features; however, the capacity of these methods to predict cognitive load is limited, suggesting that it is necessary to have knowledge of pupil size and luminance to successfully remove the pupillary light reflex. Finally, some attempts have undertaken a user-specific technique utilizing a luminance calibration process; however, requiring each new user to undergo a luminance calibration process before using a cognitive load detection feature of an XR system is likely to create friction for users who may already have to undergo several calibrations when first using a given XR product. Given the limitations of these prior attempts, examples described herein attempt to provide a user-independent, calibration-free approach to removing the influence of the pupillary light reflex in order to enable robust, PLR-corrected cognitive load detection for XR display systems, under arbitrarily varying luminance conditions, and during arbitrary user eye movement.

By providing techniques for cognitive load detection in the context of XR, examples described herein may address one or more technical problems related to XR. In some examples, the cognitive challenge level of a task presented to a user by the XR display system may be adjusted based on the detected cognitive load of the user. In some examples, a first regression model, such as a random forest regression model, may be used to predict a user's pupil size based on measured luminance, and a second regression model, such as a logistic regression model, is used to predict cognitive load based on differences between the actual measured pupil size of the user and the predicted pupil size. In some examples, more than one luminance measure may be used in predicting the user's pupil size based on the pupillary light reflex: for example, in the context of an optical see-through XR display, both the luminance of the projected light from the XR display and the ambient light from the environment may be measured and used to perform the pupil size prediction. In some examples, gaze tracking may be used to measure both local luminance at a fixation point of the user's eye as well as global luminance in the eye's peripheral vision, and both local and global luminance measures may be used to perform the pupil size prediction. Other technical solutions and features will be appreciated based on the figures, description, and claims herein.

FIG. 1 is perspective view of a head-worn XR device (e.g., glasses 100), in accordance with some examples. The glasses 100 can include a frame 102 made from any suitable material such as plastic or metal, including any suitable shape memory alloy. In one or more examples, the frame 102 includes a first or left optical element holder 104 (e.g., a display or lens holder) and a second or right optical element holder 106 connected by a bridge 112. A first or left optical element 108 and a second or right optical element 110 can be provided within respective left optical element holder 104 and right optical element holder 106. The right optical element 110 and the left optical element 108 can be a lens, a display, a display assembly, or a combination of the foregoing. Any suitable display assembly can be provided in the glasses 100. In some examples, the optical elements 108 and 110 include an optical filter as described below with reference to FIG. 3. In some examples, the optical elements 108, 110 include additional components, such as eye tracking sensors, environmental light sensors, and/or other optical sensors as described below with reference to FIG. 5.

The frame 102 additionally includes a left arm or temple piece 122 and a right arm or temple piece 124. In some examples the frame 102 can be formed from a single piece of material so as to have a unitary or integral construction.

The glasses 100 can include a computing device, such as a computer 120, which can be of any suitable type so as to be carried by the frame 102 and, in one or more examples, of a suitable size and shape, so as to be partially disposed in one of the temple piece 122 or the temple piece 124. The computer 120 can include one or more processors with memory, wireless communication circuitry, and a power source. Various other examples may include these elements in different configurations or integrated together in different ways.

The computer 120 additionally includes a battery 118 or other suitable portable power supply. In some examples, the battery 118 is disposed in left temple piece 122 and is electrically coupled to the computer 120 disposed in the right temple piece 124. The glasses 100 can include a connector or port (not shown) suitable for charging the battery 118, a wireless receiver, transmitter or transceiver (not shown), or a combination of such devices.

The glasses 100 include a first or left camera 114 and a second or right camera 116. Although two cameras are depicted, other examples contemplate the use of a single or additional (i.e., more than two) cameras. In one or more examples, the glasses 100 include any number of input sensors or other input/output devices in addition to the left camera 114 and the right camera 116, such as one or more eye tracking sensors, environmental light sensors, and/or other optical sensors as described below. Such sensors or input/output devices can additionally include location sensors, motion sensors, and so forth. In some examples, the eye tracking sensors, environmental light sensors, and/or other optical sensors can include the left camera 114 and/or right camera 116: for example, the left camera 114 and/or right camera 116 may be used as the environmental light sensor to detect ambient light, and/or as additional optical sensors to detect luminance of particular portions of the user's field of view of the real-world environment. It will be appreciated that the cameras 114, 116 are a form of optical sensor, and that the glasses 100 may include additional types of optical sensors in some examples.

Figure 2:
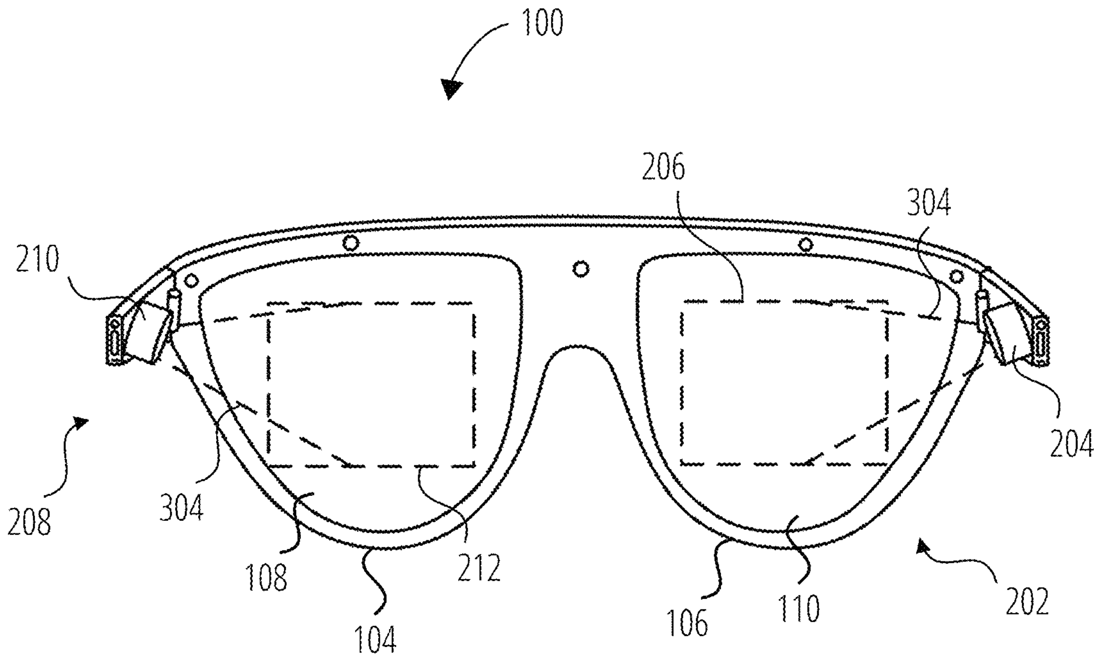
FIG. 2 illustrates a further view of the head-worn device of FIG. 1, in accordance with some examples.

FIG. 2 illustrates the glasses 100 from the perspective of a user. For clarity, a number of the elements shown in FIG. 1 have been omitted. As described in FIG. 1, the glasses 100 shown in FIG. 2 include left optical element 108 and right optical element 110 secured within the left optical element holder 104 and the right optical element holder 106 respectively.

The glasses 100 include right forward optical assembly 202 comprising a right projector 204 and a right display device 206, and a left forward optical assembly 208 including a left projector 210 and a left display device 212. The right forward optical assembly 202 may also be referred to herein, by itself or in combination with one or both of the respective optical elements 108 and 110, as a near-eye optical see-through XR display.

In some examples, the display devices 206 are waveguides. The waveguides include reflective or diffractive structures (e.g., gratings and/or optical elements such as mirrors, lenses, or prisms). Projected light 304 emitted by the projector 204 encounters the diffractive structures of the waveguide of the display device 206, which directs the light towards the right eye of a user to provide an image on or in the right optical element 110 that overlays the view of the real world seen by the user. Similarly, projected light 304 emitted by the projector 210 encounters the diffractive structures of the waveguide of the display device 212, which directs the light towards the left eye of a user to provide an image on or in the left optical element 108 that overlays the view of the real world seen by the user. The combination of a GPU, the right forward optical assembly 202, the left optical element 108, and the right optical element 110 provide an optical engine of the glasses 100. The glasses 100 use the optical engine to generate an overlay of the real world view of the user including display of a 3D user interface to the user of the glasses 100. The surface of the optical element 108 or 110 from which the projected light exits toward the user's eye is referred to as a user-facing surface or an image presentation surface of the near-eye optical see-through XR display.

It will be appreciated that other display technologies or configurations may be utilized within an optical engine to display an image to a user in the user's field of view. For example, instead of a projector 204 and a waveguide, an LCD, LED or other display panel or surface may be provided.

In use, a user of the glasses 100 will be presented with information, content and various 3D user interfaces on the near eye displays. As described in more detail herein, the user can then interact with the glasses 100 using the buttons 126, voice inputs or touch inputs on an associated device, and/or hand movements, locations, and positions detected by the glasses 100. In some examples, as described below, a user may also provide control input to the glasses 100 using eye gestures tracked by an eye tracking subsystem.

In some examples, one or more further optical lenses may be used to adjust the presentation of the virtual content to the user's eye. For example, lenses can be placed on the user-facing side and/or the exterior side of the display device (e.g., display device 206 or 212) to modulate the plane in front of the user's eye where that the virtual content appears, i.e., to adjust the perceived distance of the virtual content from the user's eye. The near user-facing side lens affects the perceived distance of the virtual content in front of the user; while the exterior side lens is provided to neutralize the effect of the near side lens on real-world objects. In some examples, an ophthalmic lens can be positioned on the user-facing side of the display device (e.g., display device 206 or 212) to allow users needing visual correction to correctly perceive the virtual content. It will be appreciated that examples described herein can be combined with various XR display designs.

Figure 3:
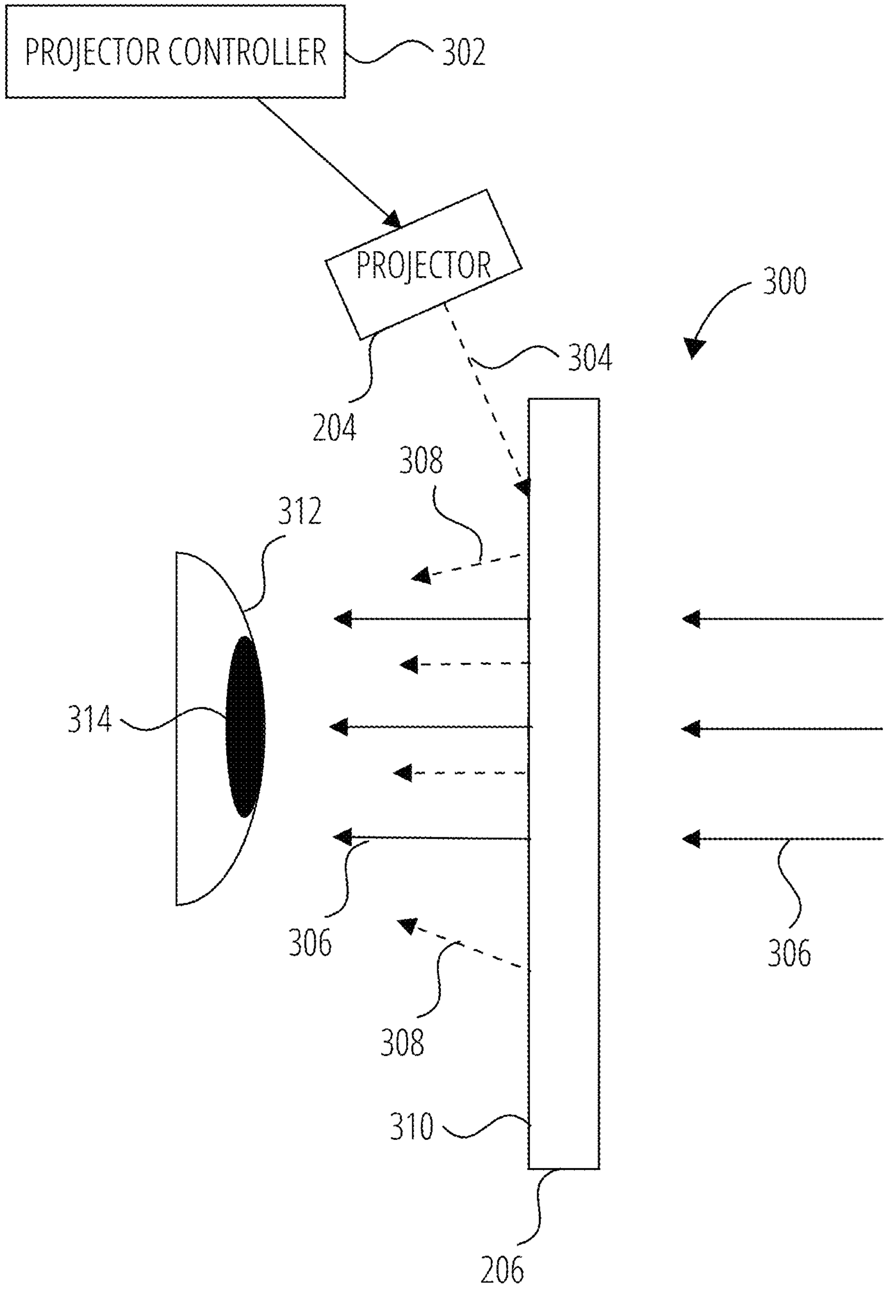
FIG. 3 is a simplified cross-sectional view of an example near-eye optical see-through XR display, in accordance with some examples.

FIG. 3 is a simplified cross-sectional view of a second example XR display 300.

The XR display 300 includes a display device 206 having an image presentation surface 310. A projector 204 is used to project visual content for presentation via the image presentation surface 310 of the display device 206; the projected light 304 emitted by the projector 204 is propagated via the display device 206 to be displayed as presented light 308 to the user's eye 312 at various locations across the image presentation surface 310. In the illustrated example, the display device 206 is an optical see-through XR display that transmits at least a portion of the environmental light 306 approaching the XR display 300 from the real-world environment to pass through to the user's eye 312. A projector controller 302 is used to control the presentation of the visual content to the user's eye 312 by the projector 204 via the display device 206.

It will be appreciated, given the shape of the eye 312 as shown in the simplified diagram of FIG. 3, that eye 312 may correspond to only a portion of the user's eyeball, such as the corneal region including the pupil 314.

The pupil 314 thus receives light from the projector 204 (as presented light 308, which corresponds to the visual content) and from the real-world environment (as environmental light 306, which corresponds to ambient light). Both of these light sources can affect the pupillary light reflex, which can complicate the detection of cognitive load, as described above.

Figure 4:
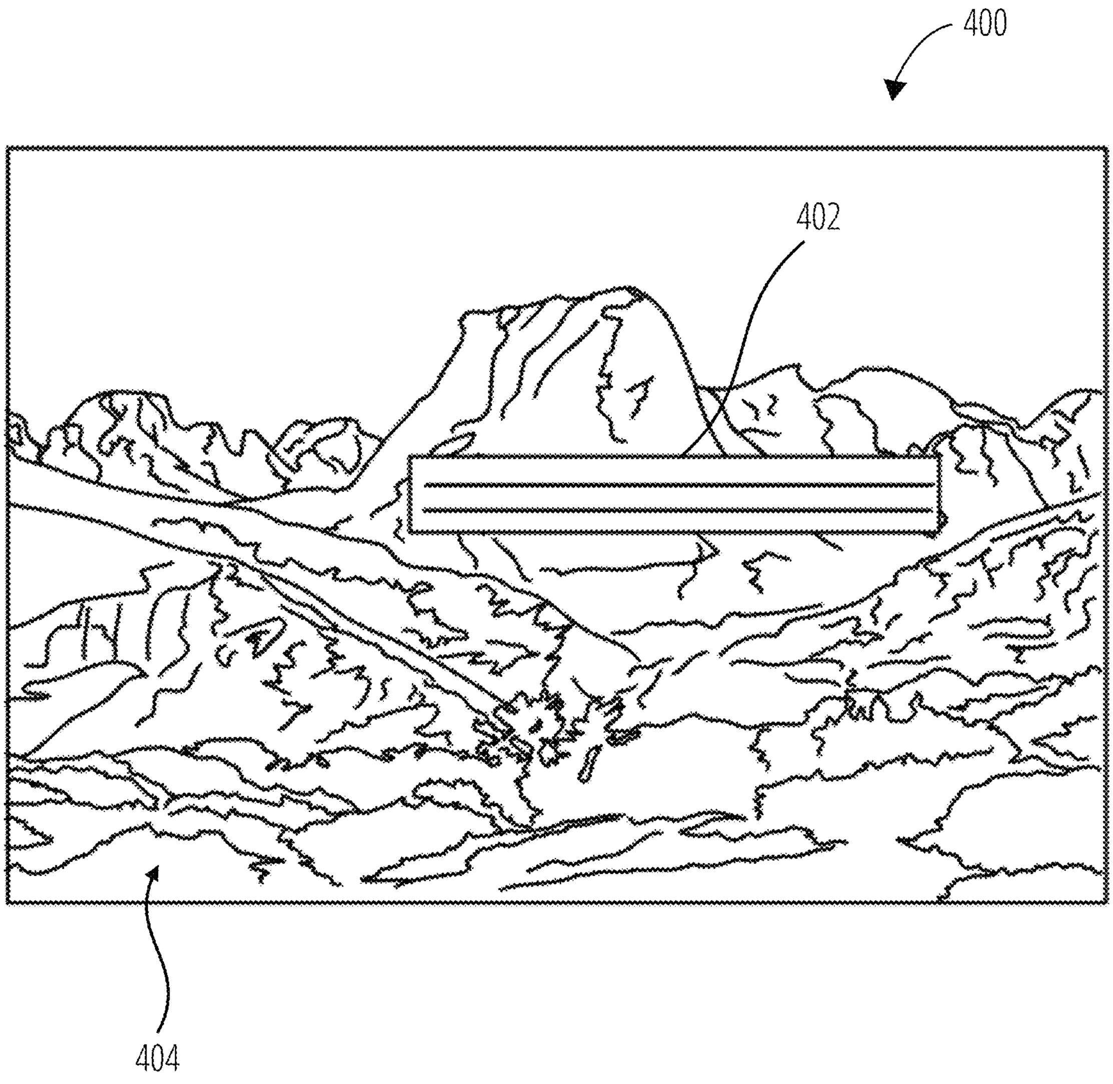
FIG. 4 illustrates an example field of view of a user’s eye through the near-eye optical see-through XR display of FIG. 3, showing virtual visual content superimposed on a real-world visual field, in accordance with some examples.

FIG. 4 shows an example field of view 400 of the user's eye 312 through the XR display 300. The field of view 400 includes a real-world visual field 404 (shown as a real-world outdoor landscape) propagated to the user's eye 312 by the environmental light 306, as well as virtual visual content 402 (shown as a rectangular graphical element) superimposed over the real-world visual field 404 due to propagation to the user's eye 312 of the presented light 308. Thus, the light entering the user's pupil 314 includes both presented light 308 corresponding to visual content (in this case, virtual visual content 402) presented by the display device 206, as well as ambient light in the form of the environmental light 306 forming the real-world visual field 404.

Figure 5:
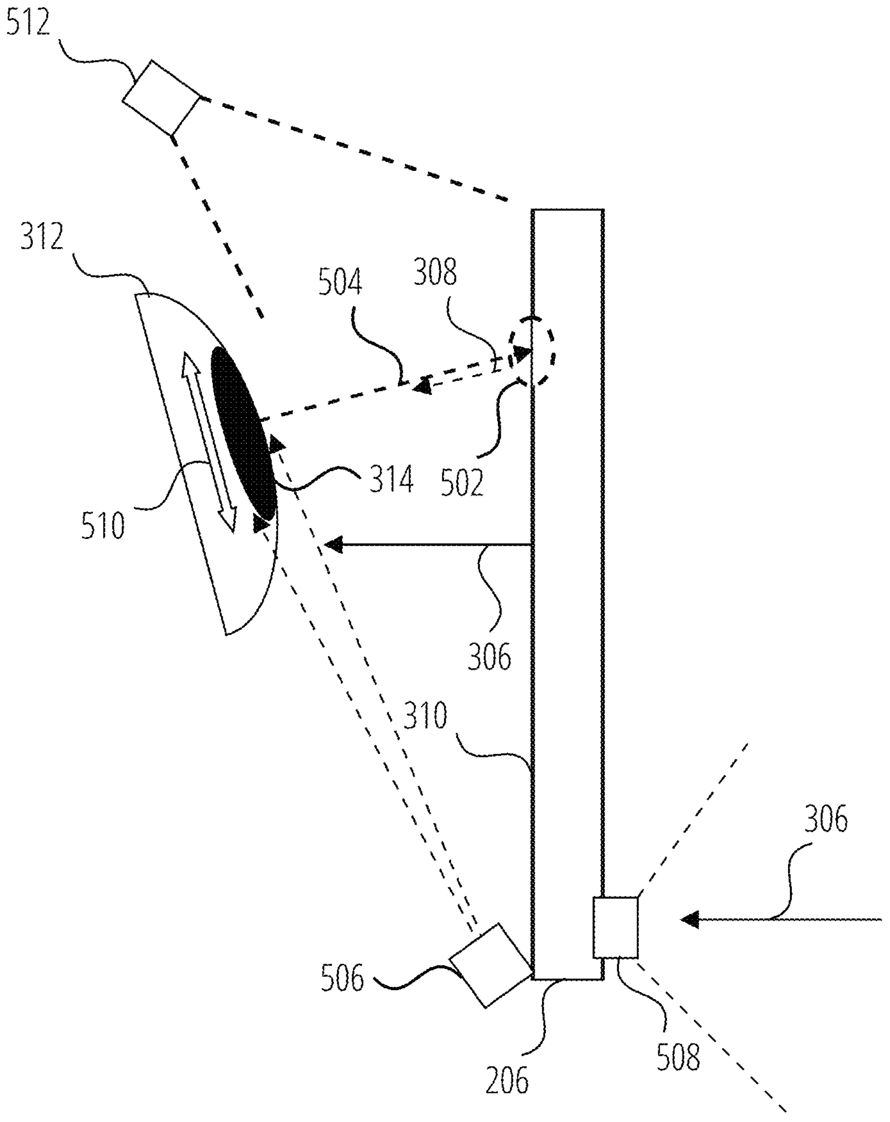
FIG. 5 is a simplified cross-sectional view of the near-eye optical see-through XR display of FIG. 3 having an eye tracking sensor and an environmental light sensor, in accordance with some examples.

FIG. 5 shows a further simplified cross-sectional view of the XR display 300. In the illustrated example, the XR display 300 includes an eye tracking sensor 506 tracking a pupil size 510 and gaze vector 504 of the eye 312, as well as two optical sensors: an environmental light sensor 508 on the world side of the display device 206 and an additional optical sensor 512 on the eye side of the display device 206. Various examples may omit the environmental light sensor 508 or the optical sensor 512, with the remaining sensor performing the functions of both as described below.

In some examples, the luminance and/or other characteristics of the environmental light 306 can be sensed by the environmental light sensor 508, as part of an environmental light subsystem described in further detail below. In some examples, the environmental light sensor 508 can be implemented by one or more of the cameras 114 and/or 116 and/or other optical sensors of the glasses 100. In some examples, the environmental light sensor 508 includes an ambient light sensor for sensing an ambient light level of the environment. In some examples, the environmental light sensor 508 includes a camera further configured to capture environmental light 306 entering the image presentation surface 310 at different locations and angles and thereby represent the real-world visual field 404 seen by the user's eye 312.

In some examples, the optical sensor 512 includes at least one camera or other optical sensor positioned on the eye side of the display device 206, facing toward the image presentation surface 310 of the display device 206 to directly capture the real-world visual field 404 (and possibly the virtual visual content 402 as well) as seen by the eye 312. Such a configuration may enable the optical sensor 512 to more accurately determine the characteristics of the environmental light 306 as it propagates through the display device 206 to the eye 312. For example, such an eye-side environmental light sensor 508 could be placed on a temple piece 122 of the glasses 100, or it could be optically coupled to the image presentation surface 310 of the display device 206 itself.

The eye tracking sensor 506 is configured to operate as part of an eye tracking subsystem, as described below, to generate pupil size data representative of the pupil size 510 of the eye 312, as well as gaze vector data representative of a gaze vector 504 of the eye 312. In some examples, each forward optical assembly (e.g., left forward optical assembly 208 and right forward optical assembly 202) of the glasses 100 includes a respective eye tracking sensor 506 for tracking the gaze vector 504 and pupil size 510 of the respective eye 312: in some such examples, a depth of gaze fixation may be determined based on the gaze vector 504 for each eye, which may assist in identifying a target of the user's visual attention in an XR visual field including visual elements perceived to be at different visual spatial depths. In some examples, the depth of gaze fixation may be detected based on the vergence angle of the eyes, or the intersection point between the left eye and right eye gaze vectors 504. However, in some examples, determining the gaze vector 504 of a single eye 312 is sufficient to determine a fixation target of the eye 312 on the two-dimensional image presentation surface 310 of the display device 206.

It will be appreciated that the pupil size 510 and gaze vector 504 of an eye can be determined using known computer vision techniques used for eye tracking. In some examples, the eye tracking sensor 506 may include one or more cameras or other optical sensors mounted to the glasses (e.g., to a user-facing side of the left forward optical assembly 208 or right forward optical assembly 202) facing inward toward the user's eye. The eye tracking sensor 506 may be an active sensor that includes one or more light-emissive elements, such as one or more visible or infrared lights for generating glints (e.g., corneal glints) on the user's eye 312 that can be detected by the optical sensor along with other visible landmarks on the eye 312, such as the pupil 314, in order to determine an angle of the gaze vector 504 relative to the angle of reflection of the glint. In some examples, the emissive elements may be arranged as a glint ring or other geometric structure around an area of the user-facing side of the left forward optical assembly 208 or right forward optical assembly 202 to improve detectability of glint positions relative to pupil positions and pupil size 510.

In some examples, the eye tracking sensor 506 uses infrared light to illuminate the eye while capturing high-speed images of the pupil 314. Software components of the eye tracking subsystem analyze the images of the eye 312 and extract the boundaries of the pupil 314. The pupil size 510 (e.g., the area and/or diameter of the pupil 314) is then calculated based on the number of pixels within the pupil boundary. This allows the eye tracking sensor 506 to provide a quantitative measure of changes in pupil size 510 in response to different stimuli or conditions. The high sampling rate of the camera of the eye tracking sensor 506 enables detecting small fluctuations in gaze direction, and/or detecting small fluctuations in pupil size 510 that may reflect cognitive processes happening in the brain, as described below.

Examples of commercially available eye tracking systems potentially usable by examples described herein include the Tobii™ Eye Tracker 5 and the eye tracking system used by the Pimax Crystal™ VR headset. In some examples, the eye tracking sensor 506 may use other means of tracking eye movements in order to determine the gaze vector 504; it will be appreciated that various eye tracking techniques are suitable for adaptation to an XR display device or system. For example, in some cases, the eye tracking data (including pupil size data and gaze vector data) may be collected and provided to the XR display system by an external source configured to track the user's gaze vector 504 and/or pupil size 510. In some examples, one or more other sensors of the XR display system, such as the left camera 114, right camera 116, and/or environmental light sensor may share one or more components with the eye tracking sensor 506: for example, a single optical sensor could be used in some cases to detect ambient light and detect glint positions and pupil positions of the user's eye 312.

In some examples, the eye tracking data generated by the eye tracking sensor 506 is representative of a respective gaze vector 504 and pupil size 510 of the user's eye 312 over each of a plurality of respective data samples collected at a plurality of points in time within a time window. Detection of cognitive load may be performed based on a plurality of such time series data samples of the user's pupil size 510, as described in further detail below. Furthermore, in some examples, gaze fixation may be determined based on a time series of data samples of the gaze vector 504 of one or both of the user's eyes.

Fixation (also called visual fixation or gaze fixation) of the eye can be detected by processing the eye tracking data to determine a gaze velocity and/or a gaze dispersion of the user's eye 312 over the time window. Gaze velocity may refer to an angular velocity of the gaze direction, and may be measured by sampling the angular displacement between gaze vectors at two or more data samples collected at points in time separated by a sampling period, and dividing the change(s) in angle by the sampling period(s) as appropriate. Gaze dispersion may refer to a conical angular range traversed by the gaze direction over a period of time, and may be measured by measuring the angular displacement between gaze vectors over a time window, then determining the greatest angular difference between any two of the number of samples measured during the time window.

In some examples, the eye 312 is determined to be fixated on a visual element (also called a visual target, a fixation target, or simply a target) if the gaze velocity is determined to be below a velocity threshold (e.g., 30 degrees per second) over a period of time (e.g., over the time window), and the gaze direction at one or more of the plurality of data samples collected at points in time over the time window intersects with the fixation target. In some examples, the eye 312 is determined to be fixated on the fixation target if the gaze dispersion is determined to be below a dispersion threshold (e.g., one degree between samples, with a sampling rate of 30 frames per second), and the gaze vector 504 of the user's eye at one or more of the plurality of data samples intersects with the fixation target.

In some examples, to determine whether the gaze vector 504 intersects with a given visual element, the XR display system may make use of a three-dimensional coordinate system for representing the virtual locations of various virtual visual elements, such as a three-dimensional coordinate system used by a video game or XR engine such as Unity™ or Lens Studio™. In some examples, the front-facing cameras 114 and 116 may also be used to detect or estimate three-dimensional locations of real-world visual elements. These virtual and real-world three-dimensional spatial maps of visual elements may be used in determining whether the gaze directions of the user's eyes intersect with various virtual and/or real-world visual elements.

In the example shown in FIG. 5, the eye 312 is angled such that the gaze vector 504 points toward a first location 502 on the image presentation surface 310 corresponding to the virtual visual content 402, as shown by the presented light 308 issuing from the image presentation surface 310 at first location 502. Thus, in the example shown in FIG. 5, it may be determined by the eye tracking subsystem that the eye 312 is fixated on the first location 502 on the image presentation surface 310 based on the eye tracking data, such as by measuring gaze velocity and/or gaze dispersion as described above. In some examples, a similar determination may be made to each of two eyes, such that corresponding fixation targets may be identified with respect to the field of view of each eye. It will be appreciated that, in binocular XR displays, a virtual visual element may be presented at respective locations on the image presentation surface 310 of each optical element 108 and 110 to indicate a single location in three-dimensional space, including an apparent spatial depth of the visual element. Thus, in some examples, the eye tracking data for two eyes may be processed to yield a highly reliable determination of gaze fixation on a fixation target.

Figure 6:
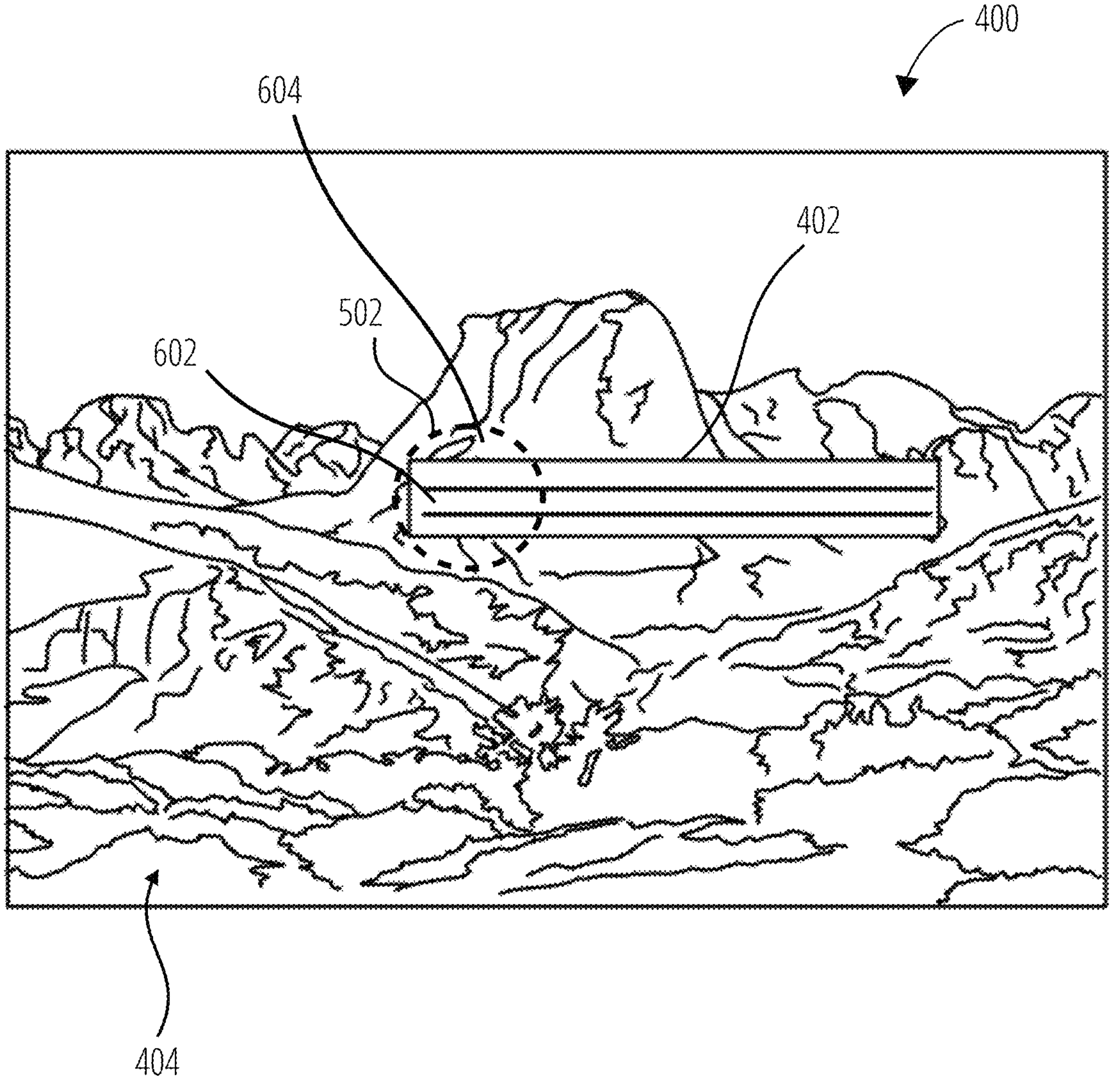
FIG. 6 illustrates a further example of the field of view of FIG. 4, showing gaze fixation on the virtual visual content, in accordance with some examples.

FIG. 6 shows the field of view 400 including the presentation of the virtual visual content 402 and the propagation of the real-world visual field 404 to the eye 312, as in FIG. 4. In this example, the first location 502 (representing the fixation target of the eye 312) is shown to correspond to part of the visual content being presented via the image presentation surface 310 (namely, a portion 602 of the virtual visual content 402) as well as a portion 604 of the real-world visual field 404 around the virtual visual content 402.

In some examples, the first location 502 is a location on the display device 206 defined by the fixation target as determined by the eye tracking subsystem. The first location 502 may be defined as a fixed portion of the field of view centered on the gaze vector 504, such as a three degree window of the field of view located within the visual field based on the vergence depth of the user's eyes. In some examples, the first location 502 may be defined at least in part based on gaze dispersion and/or gaze velocity, as described above.

Figure 7:
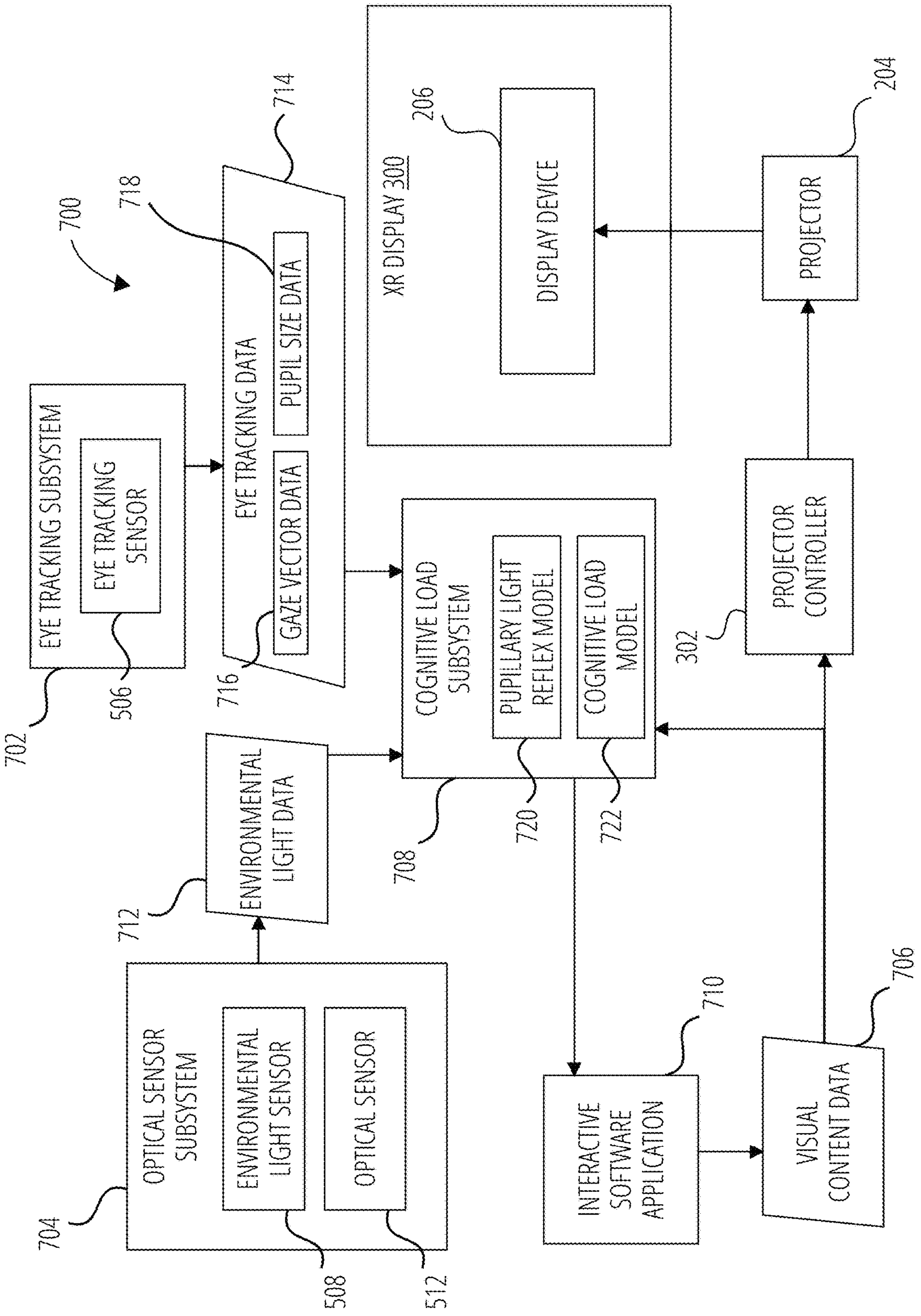
FIG. 7 is a block diagram of components of an XR display system configured to perform techniques described herein, in accordance with some examples.

FIG. 7 shows a block diagram of an example XR display system 700 configured to perform or implement the techniques described herein. The XR display system 700 includes an XR display 300, a projector 204, and a projector controller 302, as described above with reference to FIG. 3. In some examples, the XR display system 700 further includes a second XR display 300 for a second eye, which may be controlled by a second projector controller 302, or by a shared projector controller 302 used to control both XR displays 300.

The XR display system 700 also includes, in this example, an eye tracking subsystem 702, an optical sensor subsystem 704, and a cognitive load subsystem 708.

In some examples, the XR display system 700 and its subsystems may be implemented using any suitable combination of hardware and software, such as components of one or more machines 1400 described below with reference to FIG. 14.

The projector controller 302 may be configured to receive visual content data 706 representative of the virtual visual content 402, in order to project the projected light 304 toward the display device 206 in order to present the virtual visual content 402 toward the user's eye 312. The visual content data 706 may include image data, video data, three-dimensional mesh data, and/or spatial data suitable for enabling the display of the virtual visual content 402. In some examples, the visual content data 706 is a sequence of video frames (or pairs of frames, for a binocular XR display system 700) for projection by the projector 204 (or pair of projectors 204) without further processing (e.g., without further rendering of three-dimensional content into two-dimensional video frames).

The projector controller 302 is also configured to adjust the brightness and/or color of the virtual visual content 402 by adjusting the luminance of the projected light 304. In some examples, the brightness and/or color of different portions of the virtual visual content 402 may be independently adjusted, for example on a pixel-by-pixel basis. In some examples, the cognitive load subsystem 708 may use the projector controller 302 to adjust the brightness of the virtual visual content 402 or portions thereof, as further described herein, to increase or decrease the visibility, opacity, and/or salience of the virtual visual content 402.

The optical sensor subsystem 704 is configured to detect characteristics (e.g., brightness, wavelength, polarization) of light approaching the user's eye 312, and in particular the pupil 314. As described above with reference to FIG. 5, this light includes both the presented light 308 and the environmental light 306. In some examples, the environmental light sensor 508 is used to detect ambient environmental light 306 and/or the real-world visual field 404 on the world side of the display device 206. In some examples, as described below with reference to FIG. 9, the environmental light sensor 508 may be used as an ambient light sensor and/or as an RGB camera for capturing ambient light levels and/or an RGB image of the environment shown in the user's real-world visual field 404. In some examples, the optical sensor 512 is used to detect all light approaching the pupil 314 on the eye side of the display device 206, including ambient environmental light 306, the real-world visual field 404 as viewed through the display device 206 (which may occlude portions of the real-world environment), and the presented light 308 as presented over one or more locations of the image presentation surface 310. Examples that omit the optical sensor 512 may instead rely on the environmental light sensor 508 to measure the environmental light 306 only; the luminance or other characteristics of the presented light 308 may be derived from the visual content data 706 as processed by the cognitive load subsystem 708, as described below.

In some examples, the optical sensor subsystem 704 and optical sensor 512 may also be configured to confirm that the locations of the image presentation surface 310 where the virtual visual content 402 is presented correspond to the expected locations based on the visual content data 706. If the actual locations of the image presentation surface 310 where the virtual visual content 402 is presented diverge from the expected locations based on the visual content data 706, this may represent optical distortion of the projected image. In some such cases, the optical sensor subsystem 704 may measure the distortions and use these measurements to calibrate the operation of the eye tracking subsystem 702 to more accurately identify when a given fixation target corresponds to the virtual visual content 402 or to the real-world visual field 404. The information regarding optical distortion, and/or how to correct measurements to take the distortion into account, may be generated by the optical sensor 512 as calibration information and sent to the eye tracking subsystem 702 and/or the cognitive load subsystem 708.

The eye tracking subsystem 702 includes the eye tracking sensor 506, as described above. The eye tracking subsystem 702 is configured to collect eye tracking data from the eye tracking sensor 506 (or from two eye tracking sensors 506), process the eye tracking data to determine a gaze vector 504 and pupil size 510 of the eye 312 (or of two eyes) at multiple time series data samples, further process the gaze vectors 504 to determine a fixation target (or where the respective fixation targets of both eyes are located) on the image presentation surface 310 of one or both display devices 206, as described above. In some examples, the eye tracking subsystem 702 may use the calibration information generated by the optical sensor subsystem 704 to correct for optical distortion in identifying fixation targets. It will be appreciated that, in different examples, the various functions described herein as being performed by one of the subsystems or controllers of the XR display system 700 may be performed instead by one or more other subsystems or controllers.

The cognitive load subsystem 708 is configured to perform the techniques described herein by processing the various types of data and information generated by the subsystems, as well as potentially the visual content data 706, and providing the results of this processing to one or more interactive software applications 710 being executed by the XR display system 700. The interactive software applications 710 may, in turn, adjust their presentation of visual content to the user by adjusting the visual content data 706 provided to the projector controller 302. In some examples, the cognitive load subsystem 708 performs some of the cognitive load prediction operations using a pupillary light reflex model 720 and/or a cognitive load model 722, described in greater detail below.

Example methods performed by the operations of the cognitive load subsystem 708 and/or other components of the XR display system 700 are described below with reference to FIG. 8 through FIG. 10.

Figure 8:
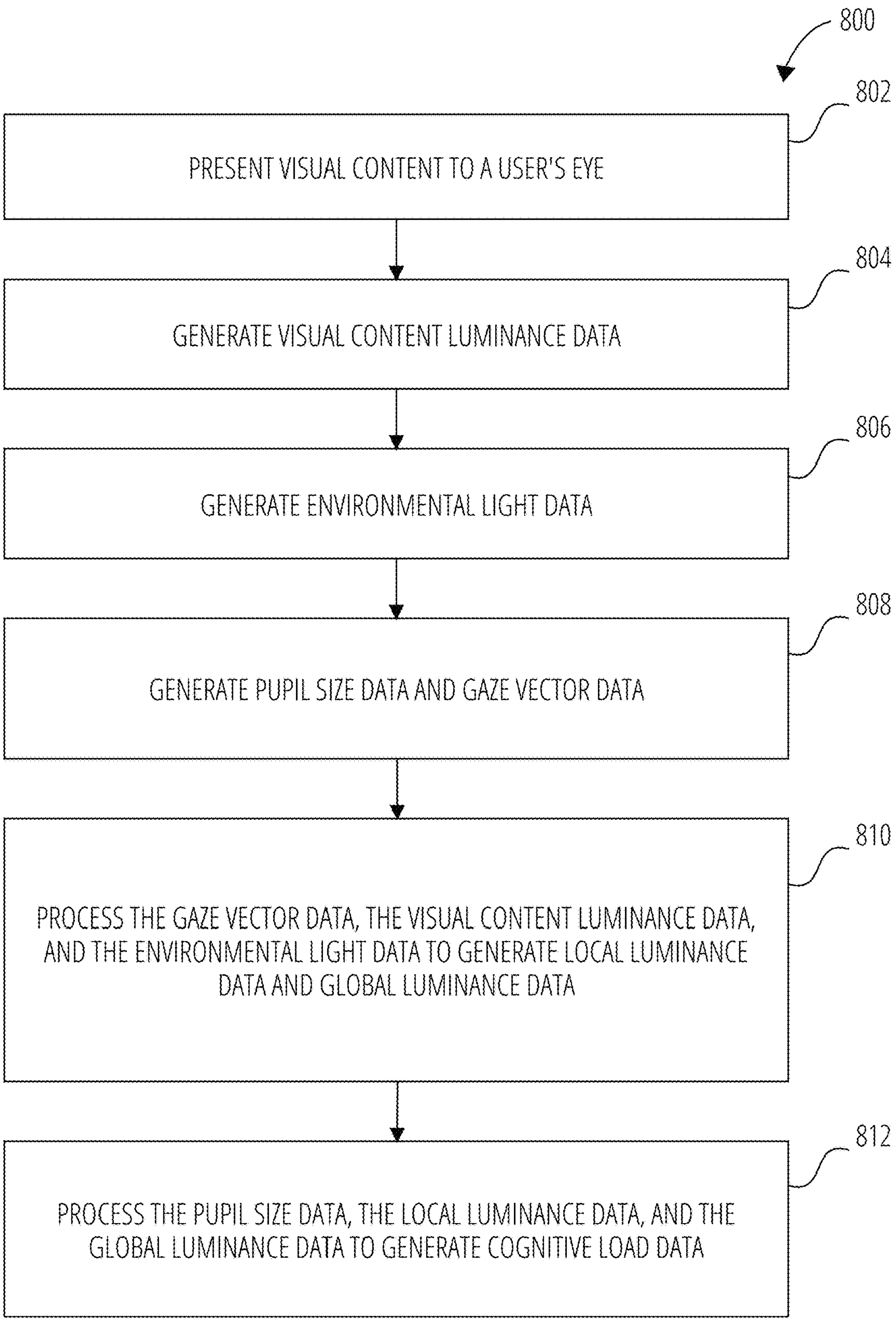
FIG. 8 illustrates a method for inferring a cognitive load of a user of an extended reality (XR) display system, in accordance with some examples.

FIG. 8 illustrates an example method 800 for inferring a cognitive load of a user of an XR display system.

The method 800 is described as being implemented by the XR display system 700. However, it will be appreciated that the operations of method 800 can be implemented or performed, in some cases, by other suitable systems or devices.

Although the example method 800 depicts a particular sequence of operations, the sequence may be altered without departing from the scope of the present disclosure. For example, some of the operations depicted may be performed in parallel or in a different sequence that does not materially affect the function of the method 800. In other examples, different components of an example device or system that implements the method 800 may perform functions at substantially the same time or in a specific sequence.

According to some examples, the method 800 includes presenting visual content (e.g., virtual visual content 402) to a user's eye 312 from a display device 206 of the XR display system 700 at operation 802. For example, an interactive software application 710 may generate visual content data 706, which used by the projector controller 302 to control the projector 204 to present the virtual visual content 402 to the eye 312.

According to some examples, the method 800 includes generating visual content luminance data representative of a luminance of the visual content as presented by the display device 206 at operation 804. In some examples, the cognitive load subsystem 708 processes the visual content data 706 to determine the luminance of the visual data as it will be presented by the projector 204 across various locations of the image presentation surface 310. In some examples, the 512 is used to measure the actual luminance of the presented light 308 from various locations across the image presentation surface 310 as it propagates from the image presentation surface 310 toward the user's eye 312. Some examples may use a combination of these two techniques, and/or other techniques, to determine luminance of the visual content at different locations. The visual content luminance data (not shown in FIG. 7) is generated by the cognitive load subsystem 708 and/or provided to the cognitive load subsystem 708 by the optical sensor subsystem 704.

According to some examples, the method 800 includes generating, by at least one optical sensor (e.g., optical sensor 512 and/or environmental light sensor 508), environmental light data 712 representative of environmental light 306 propagating toward the user's eye 312 at operation 806. The optical sensor 512 may be used to detect non-occluded environmental light 306 passing through the display device 206 toward the eye 312. The environmental light sensor 508 may be used to detect environmental light 306 as it approaches the display device 206. Either environmental light sensor 508 or optical sensor 512 (or another optical sensor such as left camera 114 or right camera 116) may be used to detect ambient environmental light 306 and/or detailed, directional environmental light 306 forming the real-world visual field 404. The environmental light data 712 is provided to the cognitive load subsystem 708.

According to some examples, at operation 808, the method 800 includes generating, by the eye tracking subsystem 702 of the XR display system 700, during the presentation of the visual content, two types of eye tracking data 714: namely, pupil size data 718 representative of a pupil size 510 of the user's eye 312, and gaze vector data 716 representative of a direction of a gaze vector 504 of the user's eye 312 (which can be processed to determine vergence depth, among other relevant measures). The eye tracking data 714 is provided to the cognitive load subsystem 708.

According to some examples, at operation 810, the method 800 includes processing the gaze vector data 716, the visual content luminance data, and the environmental light data 712 to generate local and global luminance data. Local luminance data is representative of a local luminance at the fixation target of the gaze vector 504. Global luminance data is representative of a global luminance of at least a portion of a field of view 400 of the user's eye 312 outside of the fixation target. The processing of operation 810 may be performed by the cognitive load subsystem 708, or by another subsystem of the XR display system 700 dedicated to tracking gaze fixation and luminance. Detailed sub-steps of an example of operation 810 are described with reference to FIG. 9 below. It will be appreciated that, in some examples, the processing of the gaze vector data 716, the visual content luminance data, and the environmental light data 712 to generate the local and global luminance data may be performed by means other than those described in FIG. 9.

According to some examples, at operation 812, the method 800 includes processing the pupil size data 718, the local luminance data, and the global luminance data to generate cognitive load data representative of an inferred cognitive load of the user. The processing of operation 812 is performed by the cognitive load subsystem 708. Detailed sub-steps of an example of operation 812 are described with reference to FIG. 10 below. It will be appreciated that, in some examples, the processing of the pupil size data 718, the local luminance data, and the global luminance data to generate the cognitive load data may be performed by means other than those described in FIG. 10, such as using one or more deep learning models or other statistical techniques.

Operation 802, and operations 804 through 810, may be performed for one or both of the user's eyes. If both eyes are being used to detect cognitive load, operation 812 may combine the results from both eyes, e.g., by averaging or otherwise aggregating the pupil size data and/or cognitive load data from the two eyes to infer cognitive load.

In some examples, the behavior of the XR display system 700 can be modified based on the inferred cognitive load of the user. After operation 812, method 800 may include further operations (not shown) to dynamically adapt its operation based on the inferred cognitive load of the user, such as increasing or decreasing the cognitive challenge level of a task being presented to the user. In some examples, this modification of the behavior of the XR display system 700 can be performed by providing the cognitive load data to one or more interactive software applications 710 being executed by the XR display system 700 to interact with the user. In response to detecting a low cognitive load on the user, an interactive software application 710 may increase a cognitive challenge level of a task being presented to the user: for example, an interactive software application 710 configured to teach a user how to play the plano may advance the user to a new lesson if cognitive load is inferred to be low. This may result in the interactive software application 710 adjusting the visual content data 706 to change the visual content displayed to the user, among other changes to the nature of the interaction, such as the speed of plano playing the user is prompted to follow. In some examples, an interactive software application 710 may modify its behavior to decrease the cognitive load on a user when high cognitive load is inferred. For example, the interactive software application 710 may adjust the visual content data 706 to reduce the speed or complexity of information being displayed to the user in response to detecting high cognitive load on the user. Other possible applications for the cognitive load data in the context of an adaptive XR display system 700 will be readily appreciated.

Figure 9:
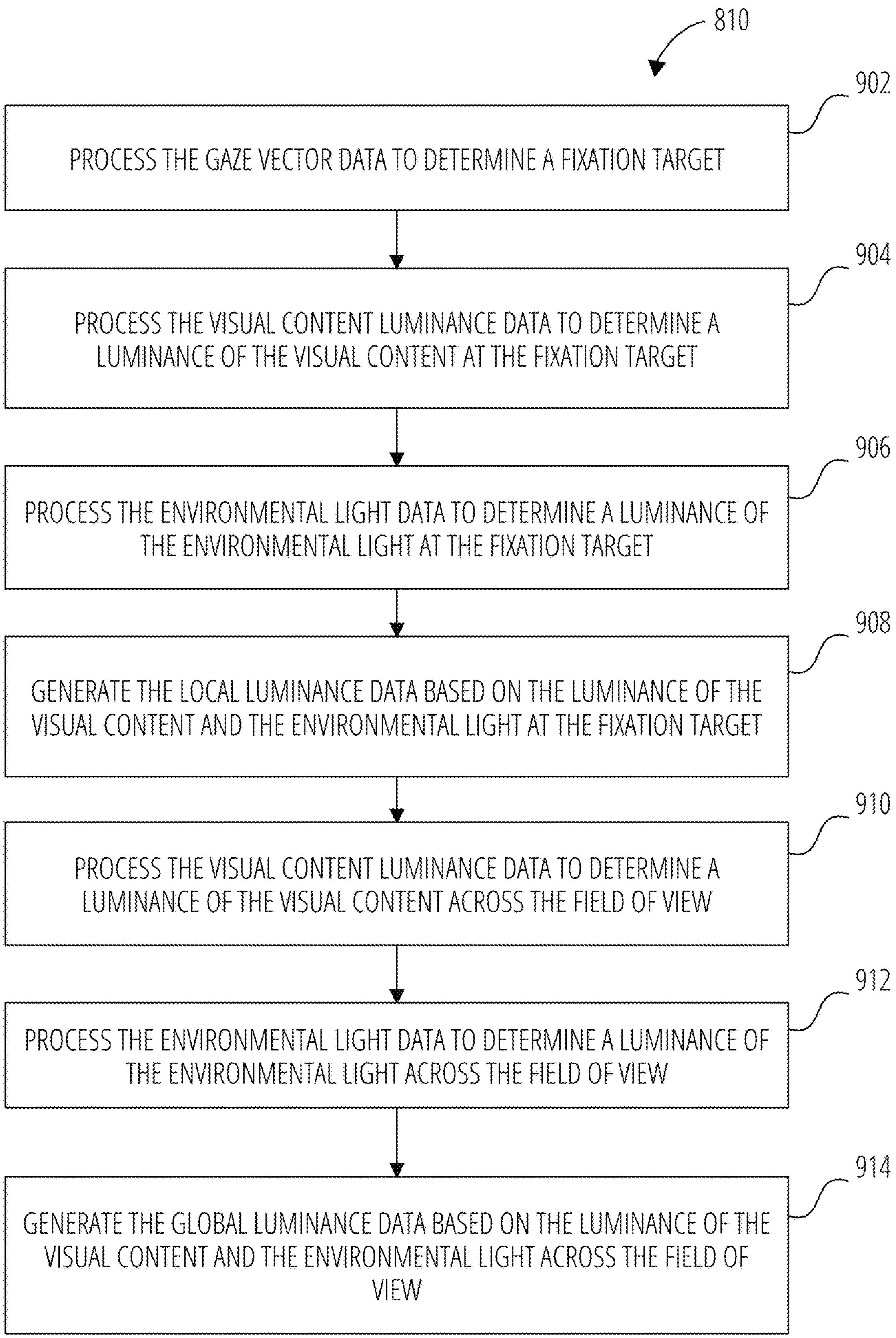
FIG. 9 illustrates operations of the step of generating local and global luminances of the method of FIG. 8, in accordance with some examples.

FIG. 9 illustrates example sub-operations of operation 810 for generating local and global luminances of method 800.

According to some examples, at operation 902, operation 810 includes processing the gaze vector data 716 to determine a fixation target on the display device 206 toward which the gaze vector 504 is directed. For example, in the field of view 400 shown in FIG. 6, the first location 502 corresponds to the fixation target. As described above, the fixation target on the display device 206 (such as first location 502) can be defined by an arc or window of the field of view 400 of the eye, such as a circular window spanning a 3 degree arc of the field of view 400.

According to some examples, at operation 904, operation 810 includes processing the visual content luminance data to determine a luminance of the visual content at the fixation target. Thus, in the example of FIG. 6, the luminance of the visual content at the fixation target can be determined as the luminance (e.g., an average luminance across multiple pixels of multiple degrees of the field of view 400) of portion 602 of the virtual visual content 402.

According to some examples, at operation 906, operation 810 includes processing the environmental light data 712 to determine a luminance of the environmental light 306 at the fixation target (such as first location 502). Thus, in the example of FIG. 6, the luminance of the environmental light 306 at the fixation target can be determined as the luminance (e.g., an average luminance across multiple pixels or multiple degrees of the field of view 400) of portion 604 of the real-world visual field 404. In some examples, operation 906 proceeds by determining local luminance at the fixation target based on sensor data from one or more optical sensors. One or more world-facing RGB cameras (e.g., cameras 114 and/or 116) capture an image of the environment. The luminance of the image(s) captured by the camera(s) is then normalized by one of two techniques. In a first technique, the cameras are calibrated to an ambient light level, such that higher RGB image values correspond to brighter regions of the image and lower RGB values correspond to darker regions of the image. In a second technique, an ambient light sensor is used to infer the ambient light level of the environment, and the inferred ambient light level is used to weight the pixel by pixel values in the image(s) produced by the RGB camera(s) such that the highest RGB values in the image(s) correspond to the output of the ambient light sensor and lower RGB values are mapped to darker luminances. Asa result, each pixel of the image(s) of the environment (corresponding to the real-world visual field 404) is mapped to a given luminance or light intensity value. These luminance values are used to infer the local luminance at the fixation target: the vergence of the user's eyes is used to determine where in the real-world visual field 404 the user is fixating (e.g., based on what visual elements the gaze vectors intersect), a 3-degree window is imposed around the point of fixation, and the portions of the image(s) within the 3-degree window have their luminance or intensity values combined (e.g., by averaging) to generate an inferred local luminance value.

According to some examples, at operation 908, operation 810 includes generating the local luminance data based on the luminance of the visual content at the fixation target and the luminance of the environmental light 306 at the fixation target. In some examples, the local luminance data includes two separate predictors: a first predictor corresponding to the luminance of the visual content at the fixation target (as derived from the visual content luminance data), and a second predictor corresponding to the luminance of the environmental light 306 at the fixation target (as derived from the environmental light data 712). In some examples, the two luminance measures may be combined, for example by averaging, weighted averaging (e.g., with respect to proximity to the center of the first location 502), or another method of aggregation or combination.

According to some examples, at operation 910, operation 810 includes processing the visual content luminance data to determine a luminance of the visual content across the field of view. This luminance measure may be computed as an average, weighted average (e.g., based on proximity to the fixation target), or total of the luminance of the visual content over multiple pixels or over one or more degrees of the field of view. Thus, in the example of FIG. 6, the luminance of the visual content across the field of view can be determined as the luminance (e.g., an average luminance across multiple pixels of multiple degrees of the field of view 400) of the entire virtual visual content 402 and any other visual content projected onto the field of view 400.

According to some examples, at operation 912, operation 810 includes processing the environmental light data 712 to determine a luminance of the environmental light 306 across the field of view. In some examples, this luminance measure may be an ambient light measure generated by the environmental light sensor 508 and/or optical sensor 512. In some examples, this luminance measure is based on environmental light 306 sensed by the environmental light sensor 508. In some examples, this luminance measure is based on environmental light 306 measured by the optical sensor 512, and therefore omits any environmental light 306 occluded by the display device 206 and/or by the visual content. Thus, in the example of FIG. 6, the luminance of the environmental light 306 across the field of view can be determined as the luminance (e.g., an average luminance across multiple degrees of the field of view 400) of the entire real-world visual field 404.

According to some examples, at operation 914, operation 810 includes generating the global luminance data based on the luminance of the visual content across the field of view 400 and the luminance of the environmental light 306 across the field of view 400. In some examples, the global luminance data includes two separate predictors: a first predictor corresponding to the luminance of the visual content across the field of view 400, and a second predictor corresponding to the luminance of the environmental light 306 across the field of view 400. In some examples, the two luminance measures may be combined, for example by averaging, weighted averaging (e.g., with respect to proximity to the first location 502), or another method of aggregation or combination.

Figure 10:
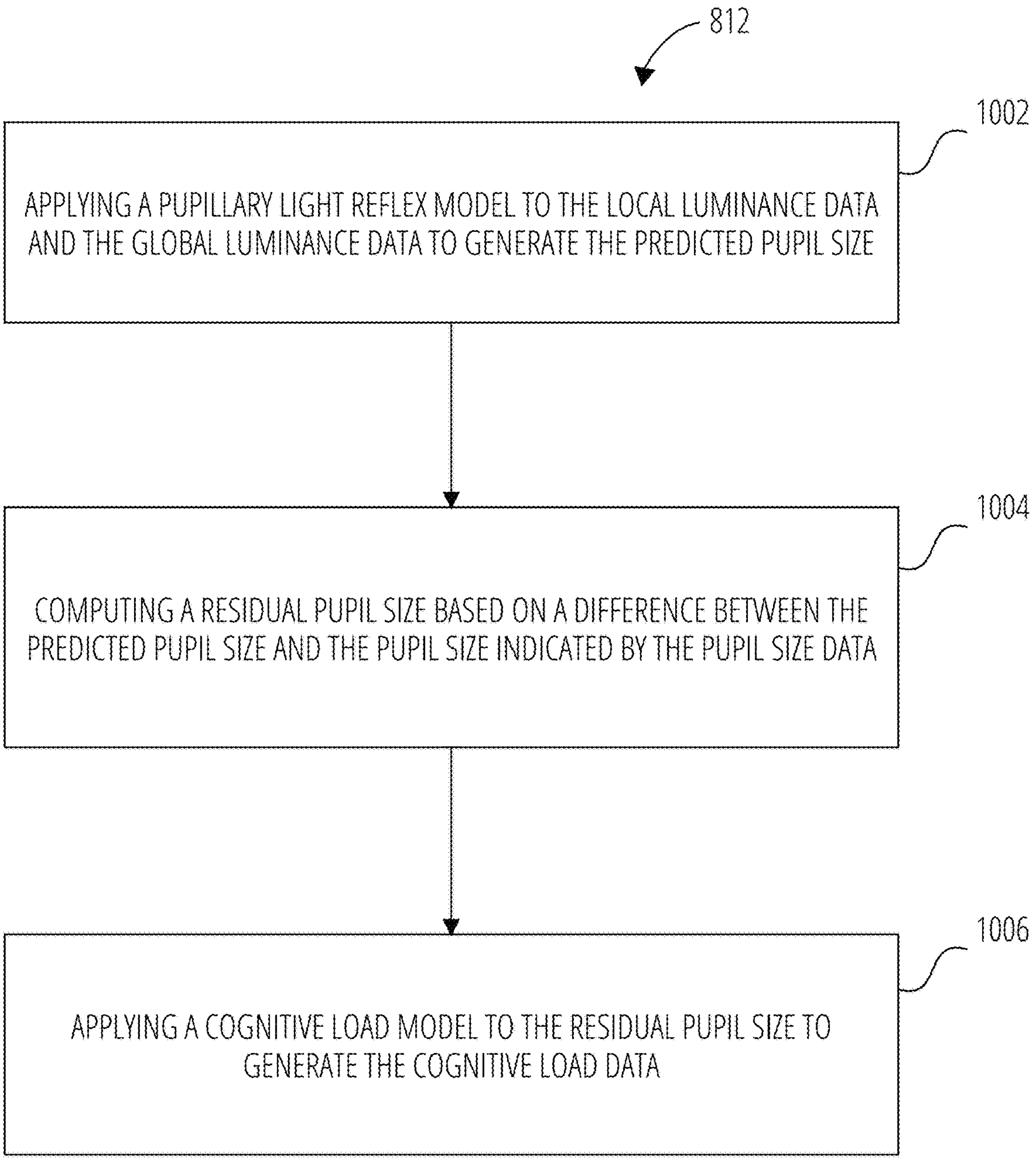
FIG. 10 illustrates operations of the step of generating cognitive load data of the method of FIG. 8, in accordance with some examples.

FIG. 10 illustrates sub-operations of the operation 812 of method 800 for generating the cognitive load data.

According to some examples, at operation 1002, operation 812 includes applying the pupillary light reflex model 720 to the local luminance data and the global luminance data to generate a predicted pupil size. In some examples, the pupillary light reflex model 720 is a regression model, such as a random forest regression model trained using random forest regression. Training of an example pupillary light reflex model 720 is described below with reference to FIG. 11 and FIG. 12, and the performance of an example trained pupillary light reflex model 720, as demonstrated through experimental testing, is described with reference to FIG. 13. In some examples, the pupillary light reflex model 720 is trained using random forest regression of the first predictor and second predictor of the local luminance data (described above) and the first predictor and second predictor of the global luminance data (also described above) on a known pupil size of a set of training data samples.

In some examples, the predicted pupil size generated by the pupillary light reflex model 720 is scaled based on a baseline pupil size of the user. Because the eye tracking subsystem 702 generates a time series of pupil size data 718, the baseline pupil size of the user may be determined by the pupil size 510 as measured prior to beginning, or at the beginning of, method 800. In some cases, taking a baseline pupil size reading will also account for individual differences in baseline pupil size that can be caused by age, drug effects, and so on. It will be appreciated that no separate calibration process is required in various examples described herein to measure the user's pupil size under various different conditions prior to commencing method 800.

The scaling of the predicted pupil size based on the baseline pupil size may take place at any of a number of different operations of operation 812 or elsewhere in method 800. In some examples, the pupillary light reflex model 720 is trained on training data samples having normalized (e.g., z-scored) pupil size measurements. Thus, normalization and/or scaling of pupil size may be performed on the pupil size data 718 and/or the predicted pupil size at various stages before, during, and/or after operation 1002 to generate an accurate predicted pupil size for the user's eye 312. For example, if the pupillary light reflex model 720 produces output that is z-scored to normalize the average pupil size prediction to 0 and the standard deviation (SD) of the pupil size prediction to 1, then the scaling may be performed at operation 1004 described below, such that the residual pupil size computed at operation 1004 may be computed based on a difference between i) the z-scored predicted pupil size and ii) a change in measured pupil size scaled to the user's baseline pupil size (e.g., a percent change in pupil size from baseline).

According to some examples, at operation 1004, operation 812 includes computing a residual pupil size based on a difference between the predicted pupil size (generated by the pupillary light reflex model 720 at operation 1002) and the pupil size 510 indicated by the pupil size data 718 generated by the eye tracking subsystem 702. In some examples, the (normalized or scaled) predicted pupil size is compared to the measured pupil size 510, and the residual pupil size is equal to a simple subtraction operation (or another difference calculation) between the two quantities. The residual pupil size represents a residual amount of pupil size not related to luminance.

According to some examples, at operation 1006, operation 812 includes applying the cognitive load model 722 to the residual pupil size to generate the cognitive load data. In some examples, the cognitive load model 722 is a regression model, such as a logistic regression model trained using logistic regression. Training of an example cognitive load model 722 is described below with reference to FIG. 11 and FIG. 12, and the performance of an example trained cognitive load model 722, as demonstrated through experimental testing, is described with reference to FIG. 13. In some examples, the cognitive load model 722 is trained using logistic regression of the residual pupil size on a known cognitive load of a set of training data samples.

Figure 11:
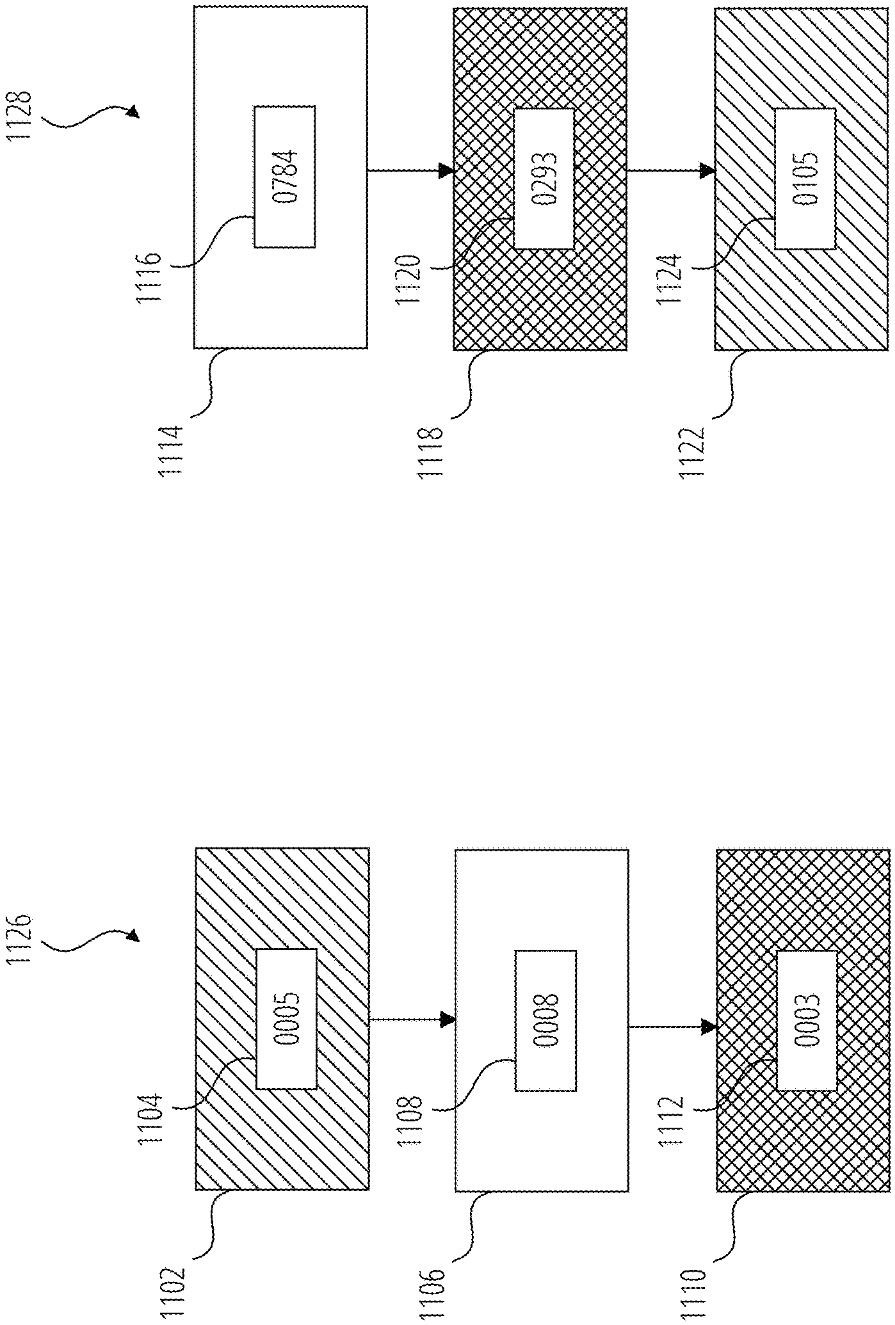
FIG. 11 illustrates two stimuli used for generating training data for models described herein, in accordance with some examples.

FIG. 11 illustrates two stimuli used for generating training data for training the pupillary light reflex model 720 and cognitive load model 722. Experimental subjects are exposed to a series of stimuli and asked to perform cognitive tasks intended to generate a varying amount of cognitive load, such as no load, low load, moderate load, and high load. Luminance conditions are also varied during the presentation of the series of stimuli. Eye tracking data 714 and luminance data are collected during each trial. The pupillary light reflex model 720 and cognitive load model 722 are then trained using the set of training data samples.

In some examples, each training data sample corresponds to a single pupil size data 718 point collected at a single point in time, associated with known local luminance data and known global luminance data for the same point in time, and a known cognitive load associated with the cognitive task being performed by the subject at the same point in time. For example, in the illustrated example of FIG. 11, subjects are asked to perform a multi-number addition task. The cognitive challenge level of the cognitive task is varied by alternating between addition of sets of three single-digit, double-digit, and triple-digit numbers, corresponding to low, moderate, and high cognitive challenge levels, respectively. Each number is presented with a local luminance in a region directly adjacent to the number itself, and a global luminance occupying the remainder of the display. Within a given task (e.g., addition of a set of three numbers), the local luminance is constant, but the local luminance is changed between tasks. The global luminance is changed between each pair of numbers presented during a single task.

FIG. 11 shows a low load stimulus 1126 consisting of a single cognitive task, namely the addition of three single-digit numbers, having a low cognitive challenge level intended to induce a low level of cognitive load in the subject. The three numbers are provided as three separate user interface screens, each number being presented for 6 seconds (6000 milliseconds (ms)). The first user interface screen (presented from 0 ms to 6000 ms of the task) has a moderate global luminance 1102 and a local luminance 1104 around the number "0005". The second user interface screen (presented from 6000 ms to 12000 ms of the task) has a high global luminance 1106 and a local luminance 1108 (equal to local luminance 1104) around the number "0008". The third user interface screen (presented from 12000 ms to 18000 ms of the task) has a low global luminance 1110 and a local luminance 1112 (equal to local luminance 1104) around the number "0003".

FIG. 11 also shows a high load stimulus 1128 consisting of a single cognitive task, namely the addition of three triple-digit numbers, having a high cognitive challenge level intended to induce a high level of cognitive load in the subject. The three numbers are provided as three separate user interface screens, each number being presented for 6 seconds (6000 milliseconds (ms)). The first user interface screen (presented from 0 ms to 6000 ms of the task) has a low global luminance 1114 (modulated by changing the light intensity of the screen background) and a local luminance 1116 around the number "0784" (modulated by changing the light intensity of the small box surrounding the number). The second user interface screen (presented from 6000 ms to 12000 ms of the task) has a low global luminance 1118 and a local luminance 1120 (equal to local luminance 1116) around the number "0293". The third user interface screen (presented from 12000 ms to 18000 ms of the task) has a moderate global luminance 1122 and a local luminance 1124 (equal to local luminance 1116) around the number "0105".

It will be appreciated that each subject may be exposed to multiple such stimuli in the course of a trial, such that a large set of different combinations of local luminance, global luminance, and cognitive load may be generated. In some examples, additional tasks may also be included in the stimuli, such as no cognitive load tasks (e.g., during rest periods between stimuli) and/or moderate cognitive load tasks (e.g., two-digit number addition).

In some examples, the local luminance and global luminance may be varied between a minimum luminance (e.g., 0.5 nits) and a maximum luminance (e.g., 200 nits) in the various stimuli. It will be appreciated that, based upon the pupillary light reflex profile, the largest change in pupil diameter will tend to occur in this range. Therefore, the models described herein may be able to generalize to outdoor luminances. The minimum and maximum luminance levels may be selected to simulate expected luminance conditions for a user of the XR display system 700 in real-world use scenarios.

Figure 12:
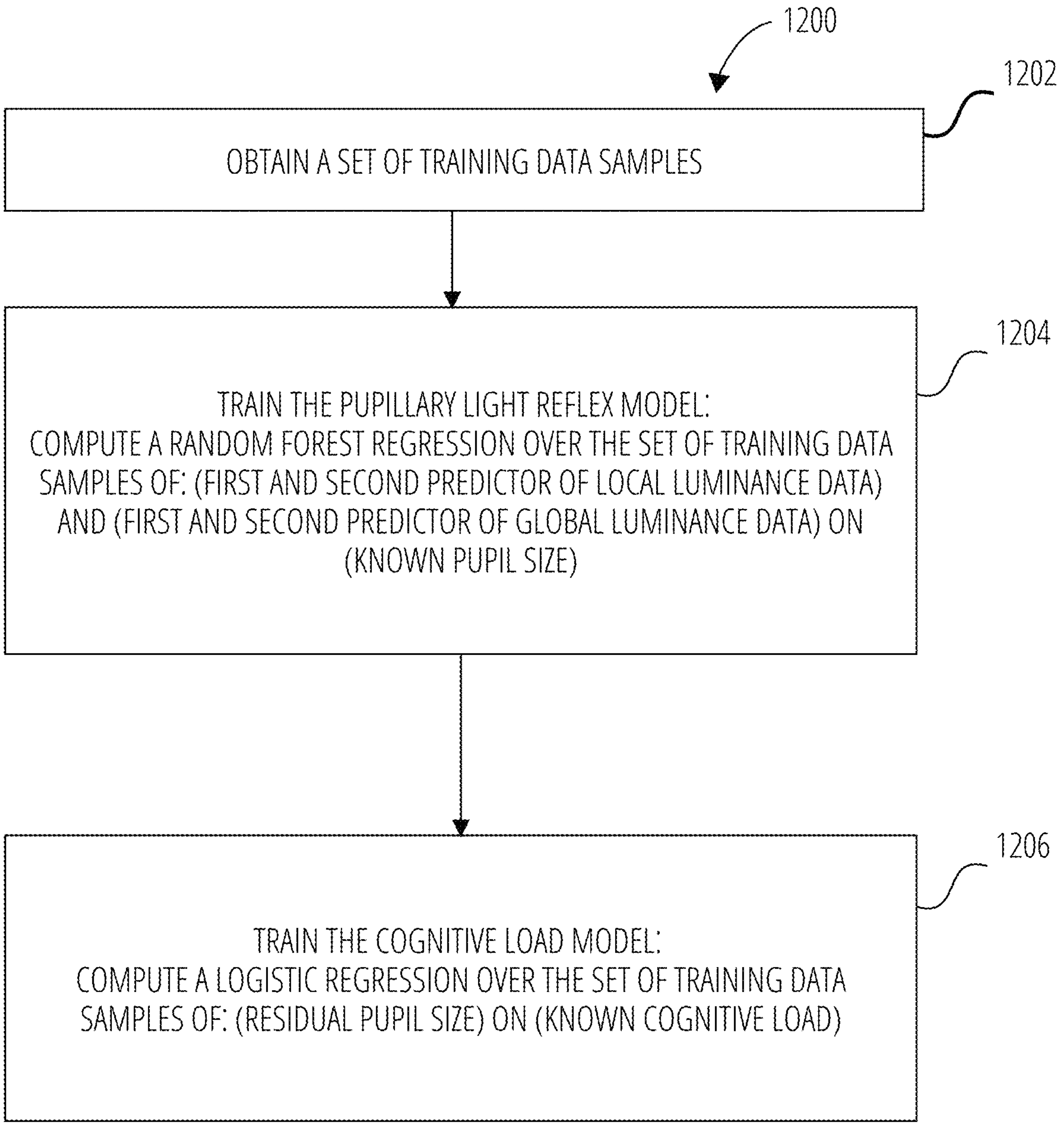
FIG. 12 illustrates a method for training models to perform the operations of the method of FIG. 8, in accordance with some examples.

FIG. 12 illustrates a method 1200 for training the pupillary light reflex model 720 and cognitive load model 722 to perform operation 812 of method 800.

Although the example method 1200 depicts a particular sequence of operations, the sequence may be altered without departing from the scope of the present disclosure. For example, some of the operations depicted may be performed in parallel or in a different sequence that does not materially affect the function of the method 1200. In other examples, different components of an example device or system that implements the method 1200 may perform functions at substantially the same time or in a specific sequence.

According to some examples, the method 1200 includes obtaining a set of training data samples at operation 1202. The training data samples may be obtained using a set of human subjects and a series of stimuli as described above with reference to FIG. 11. In some examples, other means may be used to obtain or generate training data samples that include pupil size measurements, cognitive load information, and luminance information sufficient to train the pupillary light reflex model 720 and cognitive load model 722.

According to some examples, at operation 1204, the method 1200 includes training the pupillary light reflex model 720 by computing, over the set of training data samples, a random forest regression of the luminance data variables against the pupil size data of each training data sample. Specifically, in some examples, the local luminance of each stimulus is used to represent the first predictor and second predictor of the local luminance data, the global luminance of each stimulus is used to represent the first predictor and second predictor of the global luminance data, and the four predictor variables (the first predictor and second predictor of the local luminance data and the first predictor and second predictor of the global luminance data) are regressed on a known pupil size (e.g., the pupil size 510 measured during the trials) of each training data sample using random forest regression. In some examples, only a single local luminance value and a single global luminance value are used for each training data sample, and the pupillary light reflex model 720 is trained via regression of the local luminance and global luminance on the measured pupil size 510 of each training data sample.

According to some examples, at operation 1206, the method 1200 includes training the cognitive load model 722 by computing, over the set of training data samples, a logistic regression of a residual pupil size of each training data sample on a known cognitive load of each training data sample. First, the pupillary light reflex model 720 is used to generate the predicted pupil size, and a difference between the predicted pupil size and the measured pupil size is computed, yielding the residual pupil size, as in method 800. Second, the residual pupil size computed using the trained pupillary light reflex model 720 is regressed on the known cognitive load (corresponding to the cognitive challenge level of the task of a given training data sample) to train the cognitive load model 722.

Figure 13:
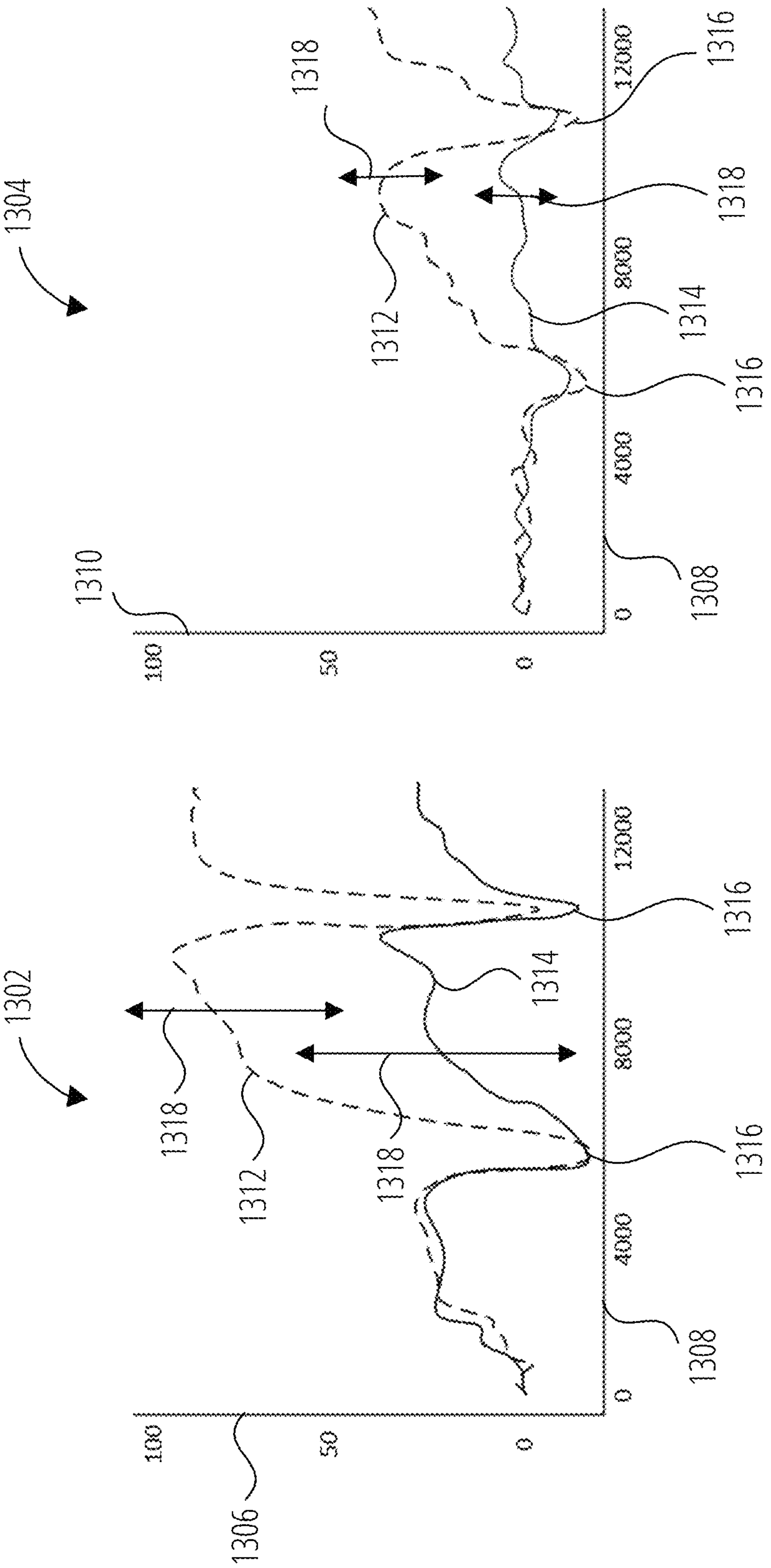
FIG. 13 illustrates graphs of raw pupil size and residual pupil size as generated by the method of FIG. 8, in accordance with some examples.

FIG. 13 illustrates a raw pupil size graph 1302 and a residual pupil size graph 1304 as generated by the eye tracking subsystem 702 and the trained pupillary light reflex model 720, respectively. This data is representative of experimental testing of an example trained pupillary light reflex model 720 and a trained cognitive load model 722.

The x-axis of each graph is time 1308 measured in ms. The y-axis of the raw pupil size graph 1302 is the change in pupil size 1306 relative to the baseline pupil size, measured as a percent increase. The y-axis of the residual pupil size graph 1304 is the change in residual pupil size 1310 relative to the baseline pupil size, measured as a percent increase.

Each graph 1302 and 1304 shows two time series: a solid line graphs the y-value of a user performing a task with a low cognitive challenge level, and a dashed line graphs the y-value of a user performing a task with a high cognitive challenge level. Error ranges 1318 show the relative sizes of the error bands for each time series of data.

It will be observed that the task with a high cognitive challenge level (high cognitive load 1312) results in a larger pupil size 510 than the task with a low cognitive challenge level (low cognitive load 1314), especially after presentation of the second number to be added, as shown in the raw pupil size graph 1302. However, the error bands of raw pupil size graph 1302 are quite large, such that the possible range of pupil sizes associated with high cognitive load 1312 and the possible range of pupil sizes associated with low cognitive load 1314 overlap significantly, thereby limiting the accuracy of predicting cognitive load without correcting for luminance.

As shown in the residual pupil size graph 1304, high cognitive load 1312 also results in a higher residual pupil size than low cognitive load 1314. However, in this case, after correcting for luminance by measuring residual pupil size after subtracting out the predicted pupil size generated by the pupillary light reflex model 720, the error ranges 1318 are much smaller than those of raw pupil size graph 1302, such that the possible range of residual pupil sizes under high cognitive load 1312 overlap very little or not at all with the possible range of residual pupil sizes under low cognitive load 1314 under many conditions.

It will be observed that, immediately after the presentation of a new user interface screen (e.g., at 6000 ms and 12000 ms), the pupil size (and residual pupil size) experiences a dip 1316, likely as a result of the pupillary light reflex due to the sudden change in luminance.

The performance of the tested models, as demonstrated by the experimental testing, indicates that the accuracy of the cognitive load model 722 after correcting for luminance using the pupillary light reflex model 720 is significantly higher than the accuracy of cognitive load detection without luminance correction. Predicting cognitive load based on the change in pupil size 1306 results in an area under the receiver operator curve (AUROC) of approximately 72% on average, and ranging from 60% to 83% over a set of training data samples. Predicting cognitive load based on the change in residual pupil size 1310, by contrast, results in an AUROC of approximately 82% on average, and ranging from 70% to 97% over the set of training data samples. It is likely that this performance could be improved by training the models using a larger dataset, and/or obtaining a training dataset with more highly calibrated luminance values (e.g., training data with distinct variables for visual content luminance and environmental light luminance, for both local and global luminance).

Machine Architecture

Figure 14:
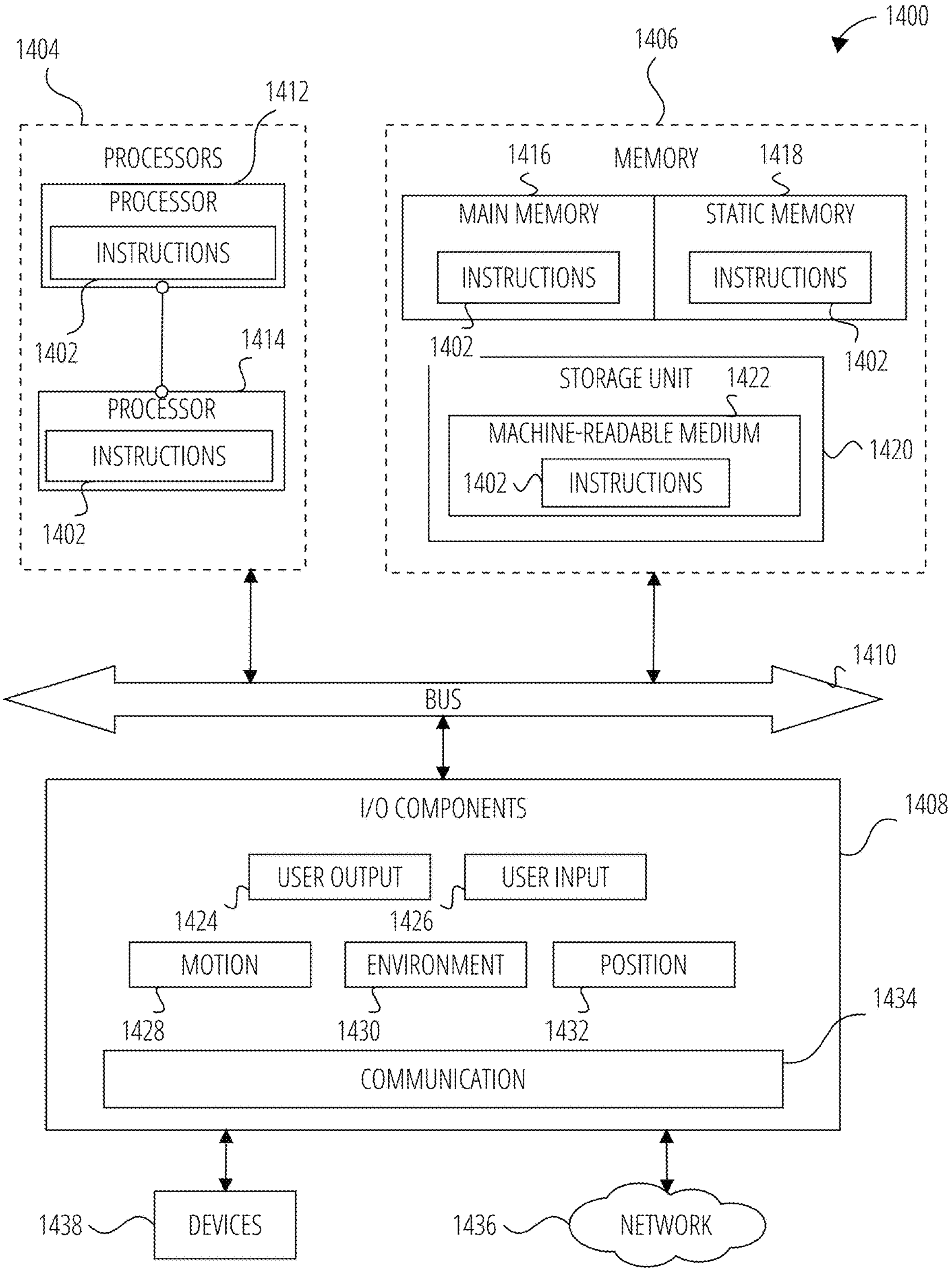
FIG. 14 is a diagrammatic representation of a machine in the form of a computer system within which a set of instructions may be executed to cause the machine to perform any one or more of the methodologies discussed herein, in accordance with some examples.

FIG. 14 is a diagrammatic representation of a machine 1400 within which instructions 1402 (e.g., software, a program, an application, an applet, an app, or other executable code) for causing the machine 1400 to perform any one or more of the methodologies discussed herein may be executed. For example, the instructions 1402 may cause the machine 1400 to execute any one or more of the methods described herein. The instructions 1402 transform the general, non-programmed machine 1400 into a particular machine 1400 programmed to carry out the described and illustrated functions in the manner described. The machine 1400 may operate as a standalone device or may be coupled (e.g., networked) to other machines. In a networked deployment, the machine 1400 may operate in the capacity of a server machine or a client machine in a server-client network environment, or as a peer machine in a peer-to-peer (or distributed) network environment. The machine 1400 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch, a pair of augmented reality glasses), a smart home device (e.g., a smart appliance), other smart devices, a web appliance, a network router, a network switch, a network bridge, or any machine capable of executing the instructions 1402, sequentially or otherwise, that specify actions to be taken by the machine 1400. Further, while a single machine 1400 is illustrated, the term "machine" shall also be taken to include a collection of machines that individually or jointly execute the instructions 1402 to perform any one or more of the methodologies discussed herein. In some examples, the machine 1400 may comprise both client and server systems, with certain operations of a particular method or algorithm being performed on the server-side and with certain operations of the particular method or algorithm being performed on the client-side.

The machine 1400 may include processors 1404, memory 1406, and input/output I/O components 1408, which may be configured to communicate with each other via a bus 1410. In an example, the processors 1404 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 1412 and a processor 1414 that execute the instructions 1402. The term "processor" is intended to include multi-core processors that may comprise two or more independent processors (sometimes referred to as "cores") that may execute instructions contemporaneously. Although FIG. 14 shows multiple processors 1404, the machine 1400 may include a single processor with a single-core, a single processor with multiple cores (e.g., a multi-core processor), multiple processors with a single core, multiple processors with multiples cores, or any combination thereof.

The memory 1406 includes a main memory 1416, a static memory 1418, and a storage unit 1420, all accessible to the processors 1404 via the bus 1410. The main memory 1406, the static memory 1418, and the storage unit 1420 store the instructions 1402 embodying any one or more of the methodologies or functions described herein. The instructions 1402 may also reside, completely or partially, within the main memory 1416, within the static memory 1418, within machine-readable medium 1422 within the storage unit 1420, within at least one of the processors 1404 (e.g., within the processor's cache memory), or any suitable combination thereof, during execution thereof by the machine 1400.

The I/O components 1408 may include a wide variety of components to receive input, provide output, produce output, transmit information, exchange information, capture measurements, and so on. The specific I/O components 1408 that are included in a particular machine will depend on the type of machine. For example, portable machines such as mobile phones may include a touch input device or other such input mechanisms, while a headless server machine will likely not include such a touch input device. It will be appreciated that the I/O components 1408 may include many other components that are not shown in FIG. 14. In various examples, the I/O components 1408 may include user output components 1424 and user input components 1426. The user output components 1424 may include visual components (e.g., a display such as the XR display 300, a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 1426 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), the eye tracking sensor 506 and eye tracking subsystem 702 for detecting eye gestures, and the like.

In further examples, the I/O components 1408 may include motion components 1428, environmental components 1430, or position components 1432, among a wide array of other components.

The motion components 1428 include acceleration sensor components (e.g., accelerometer), gravitation sensor components, rotation sensor components (e.g., gyroscope).

The environmental components 1430 include, for example, one or more externally-facing cameras (with still image/photograph and video capabilities) such as left camera 114 and right camera 116, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), depth sensors (such as one or more LIDAR arrays), or other components that may provide indications, measurements, or signals corresponding to a surrounding physical environment.

Further, the camera system of the machine 1400 may include dual rear cameras (e.g., a primary camera as well as a depth-sensing camera), or even triple, quad or penta rear camera configurations on the front and rear sides of the machine 1400. These multiple cameras systems may include a wide camera, an ultra-wide camera, a telephoto camera, a macro camera, and a depth sensor, for example. In some examples, the camera system includes the environmental light sensor 508, such as a world-facing RGB camera, and the optical sensor 512, such as a camera facing the display device 206.

The position components 1432 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1408 further include communication components 1434 operable to couple the machine 1400 to a network 1436 or devices 1438 via respective coupling or connections. For example, the communication components 1434 may include a network interface component or another suitable device to interface with the network 1436. In further examples, the communication components 1434 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1438 may be another machine or any of a wide variety of peripheral devices (e.g., a peripheral device coupled via a USB).

Moreover, the communication components 1434 may detect identifiers or include components operable to detect identifiers. For example, the communication components 1434 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph™, MaxiCode, PDF417, Ultra Code, UCC RSS-2D bar code, and other optical codes), or acoustic detection components (e.g., microphones to identify tagged audio signals). In addition, a variety of information may be derived via the communication components 1434, such as location via Internet Protocol (IP) geolocation, location via Wi-Fi® signal triangulation, location via detecting an NFC beacon signal that may indicate a particular location, and so forth.

The various memories (e.g., main memory 1416, static memory 1418, and memory of the processors 1404) and storage unit 1420 may store one or more sets of instructions and data structures (e.g., software) embodying or used by any one or more of the methodologies or functions described herein. These instructions (e.g., the instructions 1402), when executed by processors 1404, cause various operations to implement the disclosed examples, including the interactive software application 710 and the cognitive load subsystem 708.

The instructions 1402 may be transmitted or received over the network 1436, using a transmission medium, via a network interface device (e.g., a network interface component included in the communication components 1434) and using any one of several well-known transfer protocols (e.g., hypertext transfer protocol (HTTP)). Similarly, the instructions 1402 may be transmitted or received using a transmission medium via a coupling (e.g., a peer-to-peer coupling) to the devices 1438.

Software Architecture

Figure 15:
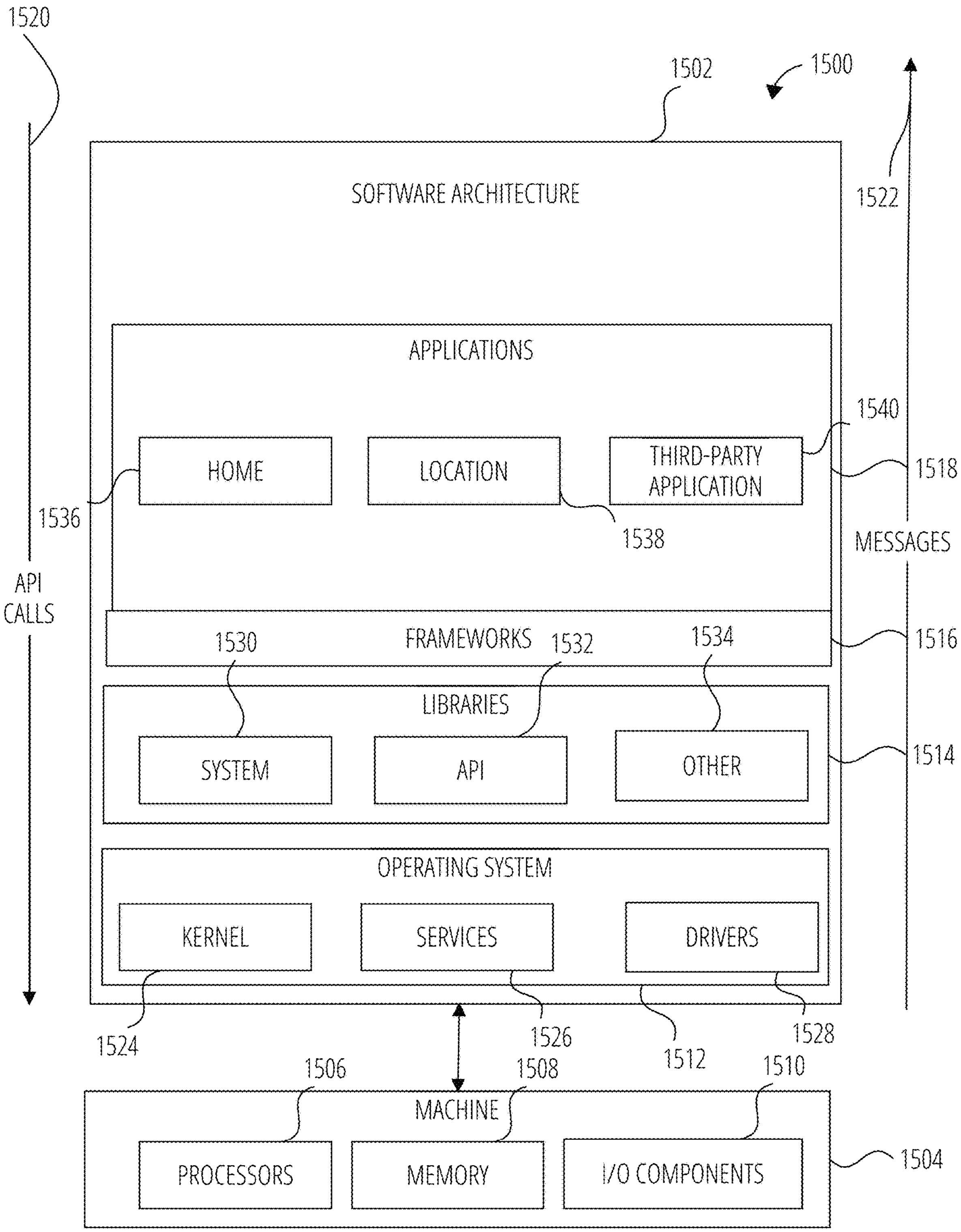
FIG. 15 is a block diagram showing a software architecture within which examples may be implemented.

FIG. 15 is a block diagram 1500 illustrating a software architecture 1502, which can be installed on any one or more of the devices described herein. The software architecture 1502 is supported by hardware such as a machine 1504 that includes processors 1506, memory 1508, and I/O components 1510. In this example, the software architecture 1502 can be conceptualized as a stack of layers, where each layer provides a particular functionality. The software architecture 1502 includes layers such as an operating system 1512, libraries 1514, frameworks 1516, and applications 1518. The applications 1518 may include one or more interactive software applications 710 as described herein. Operationally, the applications 1518 invoke API calls 1520 through the software stack and receive messages 1522 in response to the API calls 1520. The described examples and at least some of the functions of the subsystems and controllers thereof, including the projector controller 302, the cognitive load subsystem 708, and/or the interactive software application 710, may be implemented by components in one or more layers of the software architecture 1502.

The operating system 1512 manages hardware resources and provides common services. The operating system 1512 includes, for example, a kernel 1524, services 1526, and drivers 1528. The kernel 1524 acts as an abstraction layer between the hardware and the other software layers. For example, the kernel 1524 provides memory management, processor management (e.g., scheduling), component management, networking, and security settings, among other functionalities. The services 1526 can provide other common services for the other software layers. The drivers 1528 are responsible for controlling or interfacing with the underlying hardware. For instance, the drivers 1528 can include display drivers, camera drivers, BLUETOOTH® or BLUETOOTH® Low Energy drivers, flash memory drivers, serial communication drivers (e.g., USB drivers), WI-FI® drivers, audio drivers, power management drivers, and so forth.

The libraries 1514 provide a common low-level infrastructure used by the applications 1518. The libraries 1514 can include system libraries 1530 (e.g., C standard library) that provide functions such as memory allocation functions, string manipulation functions, mathematic functions, and the like. In addition, the libraries 1514 can include API libraries 1532 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 1514 can also include a wide variety of other libraries 1534 to provide many other APIs to the applications 1518.

The frameworks 1516 provide a common high-level infrastructure that is used by the applications 1518. For example, the frameworks 1516 provide various graphical user interface (GUI) functions, high-level resource management, and high-level location services. The frameworks 1516 can provide a broad spectrum of other APIs that can be used by the applications 1518, some of which may be specific to a particular operating system or platform.

In an example, the applications 1518 may include a home application 1536, a location application 1538, and a broad assortment of other applications such as a third-party application 1540. The applications 1518 are programs that execute functions defined in the programs. Various programming languages can be employed to create one or more of the applications 1518, structured in a variety of manners, such as object-oriented programming languages (e.g., Objective-C, Java, or C++) or procedural programming languages (e.g., C or assembly language). In a specific example, the third-party application 1540 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the third-party application 1540 can invoke the API calls 1520 provided by the operating system 1512 to facilitate functionalities described herein.

The models and techniques described above provide an approach to PLR correction in detecting cognitive load that relies on only two measures of luminance—local luminance and global luminance—to train and deploy a system capable of detecting cognitive load in an arbitrary user. However, further refinements of the techniques described above can be provided in some examples.

In some examples, a lag parameter can be modeled by the pupillary light reflex model 720. Experimental testing indicates that there is typically a lag of approximately 500 ms between a change in light properties and a corresponding change in pupil size due to PLR. Although this lag parameter shows a significant amount of uniformity among individual human subjects, it can vary somewhat across individuals, as well as varying between different types of change in light properties. Thus, in some examples, a separate lag parameter is associated with each light parameter (e.g., one lag parameter for global luminance and a separate lag parameter for local luminance), and/or a separate lag parameter or set of lag parameters are associated with each distinct human user, in the pupillary light reflex model 720. The values of the lag parameters can be expected to vary between approximately 400 ms and 600 ms.

In some examples, the two measures of luminance are supplemented with additional data encoding or representative of one or more additional parameters corresponding to characteristics of the light reaching the user's eye. These additional parameters can include one or more of the following, in addition to the local luminance and global luminance parameters:

1. A local root mean square (RMS) contrast parameter representative of a variation of luminance in a region of the user's field of view where the user's gaze is directed. For example, the local RMS contrast parameter can be computed as a root mean square luminance difference in pixels captured by a camera within the local region where the user's gaze is fixated (e.g., a 3 degree window or circle around the gaze direction or point of gaze fixation).
2. A global RMS contrast parameter representative of a variation of luminance across the user's field of view.
3. A local Michelson contrast parameter representative of a difference between a highest and a lowest value of luminance in a region of the user's field of view where the user's gaze is directed. For example, the local Michelson contrast parameter can be computed as a luminance difference between the highest-luminance pixel and the lowest-luminance pixel captured by a camera within the local region where the user's gaze is fixated.
4. A global Michelson contrast parameter representative of a difference between a highest and a lowest value of luminance across the user's field of view.
5. A target-to-local Weber contrast parameter representative of a difference in luminance between a target of the user's gaze and a region of the user's field of view surrounding the target of the user's gaze. For example, the target-to-local Weber contrast parameter can be computed as a difference between the measured luminance at the point of gaze fixation and the local luminance. In some examples, target-to-local Weber contrast can be calculated as ([I−Ib]/Ib), where I represents the luminance of the features at the point of gaze fixation and Ib represents the luminance of the local background.

6. A local-to-global Weber contrast parameter representative of a difference in luminance between a region of the user's field of view surrounding a target of the user's gaze and the user's entire field of view. For example, the local-to-global Weber contrast parameter can be computed as a difference between the local luminance and the global luminance. In some examples, local-to-global Weber contrast can be calculated as ([I−Ib]/Ib), where I represents the luminance of the features at the local region and Ib represents the luminance of the global background.
7. A global blue parameter representative of an amount of blue light in the user's field of view. For example, the global blue parameter can be computed as the global luminance calculated using only the blue pixel values of a set of RGB pixels. In some examples, color parameters (such as the global blue parameter) can be modeled by the chromaticity in another coordinate system, such as 1931 CIELAB.
8. A global green parameter representative of an amount of green light in the user's field of view. For example, the global green parameter can be computed as the global luminance calculated using only the green pixel values of a set of RGB pixels.
9. A global red parameter representative of an amount of red light in the user's field of view. For example, the global red parameter can be computed as the global luminance calculated using only the red pixel values of a set of RGB pixels.

It will be appreciated that the nine additional parameters described above can all be derived from the same data sources as the local luminance and global luminance, namely, the environmental light data 712, the visual content luminance data (derived from the visual content data 706 and/or the environmental light data 712), and the eye tracking data 714.

Thus, in some examples, the pupillary light reflex model 720 is expanded to include 11 parameters: the local luminance parameter, the global luminance parameter, and the nine additional parameters listed above. Other examples may also include other scene parameters capturing different characteristics of the light presented to the user's eyes, or may include only a subset of the additional parameters in the model. For example, further scene parameters used in the model can include local and/or global temporal contrast (representative of a temporal change in luminance either within the local window or across the field of view), and/or local and/or global edge density (representative of spatial frequency of spatial changes in luminance across the local window or the entire field of view). Each parameter used by the pupillary light reflex model 720 can be associated with a distinct lag parameter in some examples.

Figure 16:
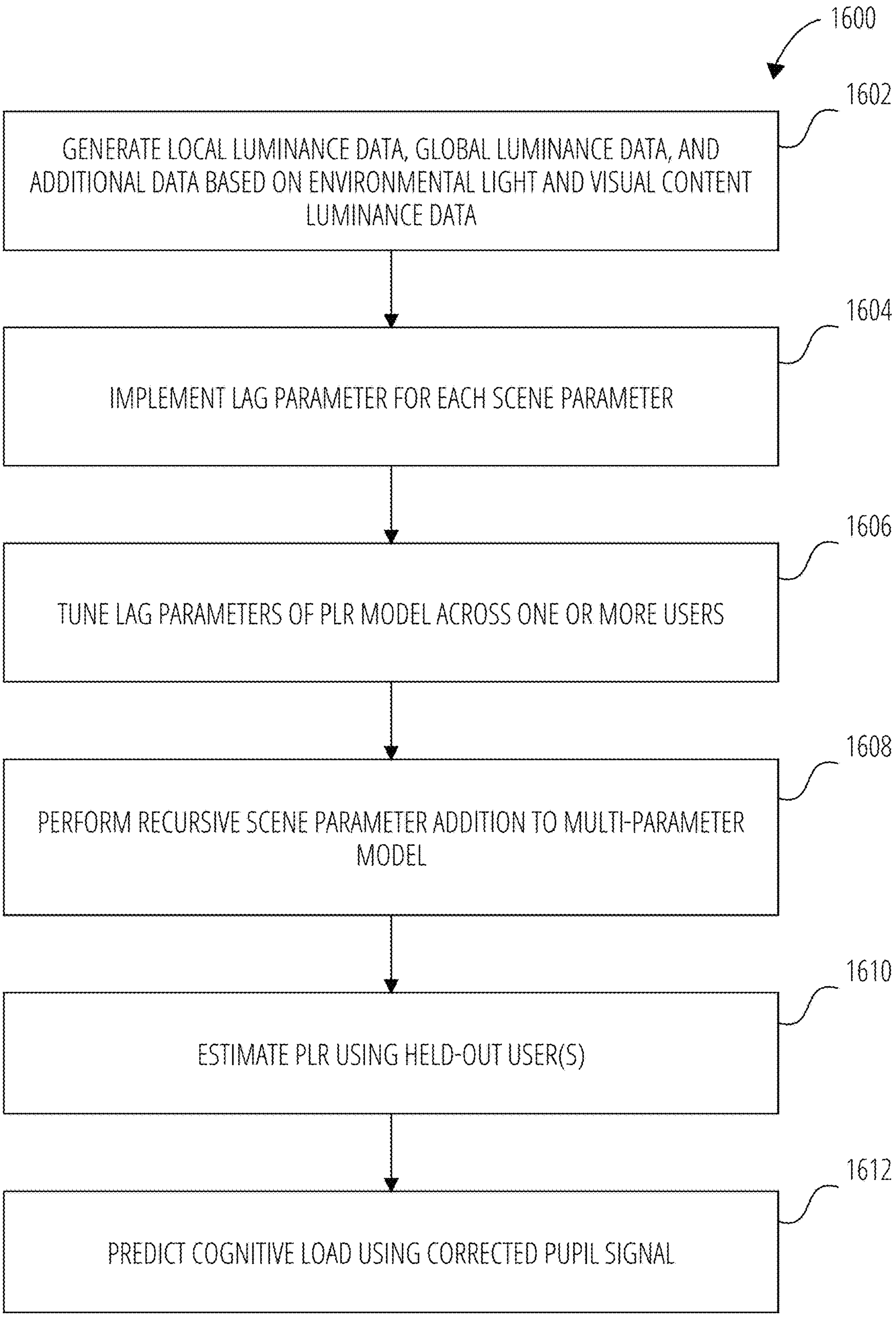
FIG. 16 illustrates a method for further user-specific training of a pupillary light reflex model, in accordance with some examples.

FIG. 16 illustrates a method 1600 for training of a pupillary light reflex model using multiple scene parameters. In some examples, a multi-parameter pupillary light reflex model is trained using random forest regression by recursively adding scene parameters until a trained or optimized model is provided in which those scene parameters with predictive powers are included and other parameters are excluded or given low weights in the prediction process. In other examples, the model can be trained using any suitable methodology to capture interactivities and nonlinearities in the relations between parameters.

Although the example method 1600 depicts a particular sequence of operations, the sequence may be altered without departing from the scope of the present disclosure. For example, some of the operations depicted may be performed in parallel or in a different sequence that does not materially affect the function of the method 1600. In other examples, different components of an example device or system that implements the method 1600 may perform functions at substantially the same time or in a specific sequence.

According to some examples, the method 1600 includes generating the scene parameters, including the local luminance data, the global luminance data, and one or more of the additional parameters of additional data based on environmental light and visual content luminance data at operation 1602. The local luminance data and global luminance data can be generated according to operation 810 as described above with reference to FIG. 9. The additional data can include one or more of the additional parameters, computed as described above.

According to some examples, the method 1600 includes implementing a respective lag parameter for each scene parameter at operation 1604. In some examples, the scene parameters include the eleven parameters described above, and may also include one or more further parameters (such as local and/or global temporal contrast and/or spatial frequency parameters). The training method 1600 can optimize the performance of the pupillary light reflex model 720 by determining which parameters to use for pupil size prediction, and/or how much weight to give to each parameter, as described below.

According to some examples, the method 1600 includes tuning the lag parameters of the PLR model to predict pupil behavior across one or more users at operation 1606. In some examples, the lag hyperparameter tuning operation 1606 uses data from a subset of users, such as data from N−1 users out of a training group of N users. The operation 1606 can employ a nested cross-validation approach to optimize the model's performance in estimating the pupillary light reflex (PLR) across multiple individual human subjects. The nested cross-validation approach involves training the model on data from the selected users (e.g., the N−1 users), allowing for a more generalized model that can potentially work for new, unseen users without requiring individual calibration. Inner cross-validation (e.g., inner 7-fold cross-validation) can be used to fine-tune the lag parameter for each scene parameter, optimizing the model's ability to capture the time delay between visual stimuli and pupillary response across a diverse set of users.

According to some examples, the method 1600 includes performing recursive feature addition to the user-specific model at operation 1608. "Features" refers to the scene parameters and/or other parameters used by the model to predict PLR. Following the lag hyperparameter tuning operation 1606, the recursive feature addition operation 1608 is conducted for the multi-parameter PLR model. In some examples, the recursive feature addition operation 1608 is conducted on a subset of the users (e.g., the N−1 users) using the same nested cross-validation structure with an inner 7-fold CV. This process systematically evaluates the importance of each scene parameter by iteratively adding them to the model and assessing their impact on performance across multiple users. The nested cross-validation approach ensures that feature selection is performed robustly, minimizing the risk of overfitting and producing a generalized set of features that best predict the pupillary light reflex (PLR) across a diverse group of users. By selecting features that work well for multiple individuals, this process aims to create a robust group model that can effectively estimate the PLR for new, unseen users without requiring individual calibration.

By conducting this tuning and recursive scene parameter addition on N−1 users, a robust group model can be trained that can effectively estimate the PLR for new users, potentially improving the accuracy of cognitive load detection without user-specific calibration or training.

According to some examples, the method 1600 includes estimating PLR for the held-out user or users at operation 1610. In some examples, the multi-parameter group-trained PLR model estimates the PLR for the held-out user (e.g., the Nth user), applying the optimized group model with tuned lag parameters and selected features to predict the PLR for a new, unseen individual. This step can assist in assessing the model's generalization ability and validating its performance in predicting pupillary responses for users who were not part of the training set. By estimating the PLR on a held-out user or users, the performance of the group model can be evaluated in a calibration-free scenario, potentially enabling accurate cognitive load detection for new users without requiring individual calibration or extensive training data.

According to some examples, the method 1600 includes predicting cognitive load for the held-out user or users using the corrected pupil signal at operation 1612. This operation allows the accuracy of the end-to-end PLR-corrected cognitive load detection process to be evaluated for validation against the ultimate goal of cognitive load prediction (or prediction of another task-evoked pupillary response, such as frustration or engagement as described above).

Once the multi-parameter group-trained PLR model has been trained using method 1600, it can be deployed as the pupillary light reflex model 720 to perform operation 1002 as described above with reference to FIG. 10. In experimental testing, a multi-parameter group-trained PLR model trained according to method 1600 on data from a group of 55 users has been shown to exhibit a more than 11% improvement in the accuracy of the end-to-end cognitive load detection process relative to a cognitive load model without PLR correction. It will be appreciated that larger training user groups may yield greater improvements in performance.

Experimental testing was also performed using scene parameter such as gaze velocity and saccades; however, these exhibited very little predictive power under test conditions when incorporated into the pupillary light reflex model 720.

In some examples, a calibration procedure is performed prior to an XR session, such as when a user first dons and activates the glasses 100. Whereas the examples above provide a calibration-free technique for PLR correction for detecting cognitive load, in some examples a per-session or per-user calibration is performed to calibrate the pupillary light reflex model 720 prior to use. The calibration procedure can include presentation of a calibration stimulus to the user's eye via the display device 206, while using the eye tracking sensor 506 to obtain pupil size information representative of the size of the pupil (referred to as calibration pupil size data). For example, the user can be prompted to look at the display device 206 while the luminance displayed on the display device 206 is changed over a range or sequence of different values. The user's pupil size is recorded as calibration pupil size data during presentation of each of these luminance values. The calibration pupil size data can then be processed to generate user pupillary light reflex data representative of the pupillary light reflex of the user's eye in response to the calibration stimulus: for example, after plotting the pupil size (e.g., diameter d) against luminance Y (lagged by a lag parameter, e.g., 500 ms) for multiple values of Y, a curve can be fitted to the resulting data such that $d(Y)=a\cdot e^{b-Y}+c$, by solving for a, b, and c.

Figure 17:
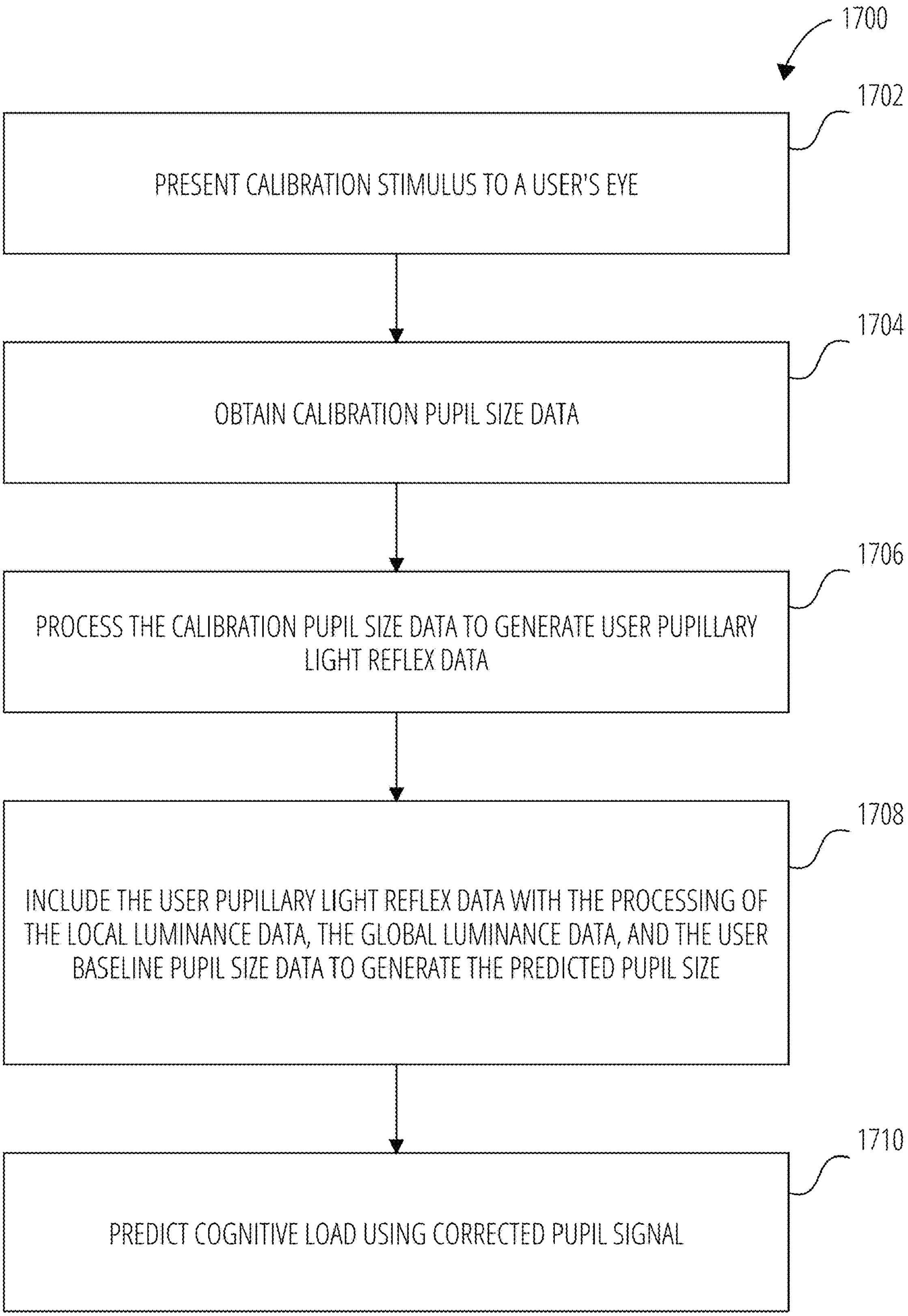
FIG. 17 illustrates a method for calibrating an XR display system, in accordance with some examples.

FIG. 17 illustrates a method 1700 for calibrating an XR display system. The method 1700 is referred to herein as a calibration procedure.

The method 1700 is described as being implemented by the XR display system 700. However, it will be appreciated that the operations of method 1700 can be implemented or performed, in some cases, by other suitable systems or devices.

Although the example method 1700 depicts a particular sequence of operations, the sequence may be altered without departing from the scope of the present disclosure. For example, some of the operations depicted may be performed in parallel or in a different sequence that does not materially affect the function of the method 1700. In other examples, different components of an example device or system that implements the method 1700 may perform functions at substantially the same time or in a specific sequence.

According to some examples, the method 1700 includes presenting a calibration stimulus to a user's eye at operation 1702. As described above, the calibration stimulus can be a sequence or continuous range of luminance values applied to the user's eye via the display device 206. In some examples, the calibration stimulus may include further or more complex stimuli; however, the experimental testing results described herein use a calibration procedure lasting less than one minute, with uniform luminances used for the calibration stimulus.

According to some examples, the method 1700 includes obtaining calibration pupil size data at operation 1704. The eye tracking sensor 506 is used to measure pupil size while the calibration stimulus is being presented.

According to some examples, the method 1700 includes processing the calibration pupil size data to generate user pupillary light reflex data at operation 1706. By plotting the pupil size against the luminance (after applying a lag parameter to the timing of the luminance changes), a curve can be fitted to the data to generate user pupillary light reflex data (e.g., a set of scalar values a, b, and c as described above).

According to some examples, the method 1700 includes processing the user pupillary light reflex data along with the processing of the local luminance data, the global luminance data, and the user baseline pupil size data to generate the predicted pupil size at operation 1708. In the example above, the user pupillary light reflex data can be used to predict the pupil size of the eye at time (t+lag parameter) following the presentation of a given luminance value at time t (for example, $d(Y)=a\cdot e^{-b-Y}+c$). In some examples, operation 1708 is used to modify sub-operation 1002 of operation 812 of method 800, described above in reference to FIG. 10: the predicted pupil size can be generated at operation 1002 based not only on the local luminance and global luminance (as well as optionally, the additional data described above), but also the user pupillary light reflex data generated at operation 1706.

According to some examples, the method 1600 includes predicting cognitive load for the held-out user or users using the corrected pupil signal at operation 1710. This operation allows the accuracy of the end-to-end PLR-corrected cognitive load detection process to be evaluated for validation against the ultimate goal of cognitive load prediction (or prediction of another task-evoked pupillary response, such as frustration or engagement as described above). In some examples, a calibration procedure as described above is used in place of the pupillary light reflex model 720 to predict pupil size based on luminance (e.g., global luminance or local luminance). In other examples, the calibration procedure is used to provide a baseline PLR prediction for a given user, which is then adjusted using a multi-parameter pupillary light reflex model 720 as described above.

In experimental testing, a stand-alone PLR model generated by the calibration procedure described above is used to provide more than 9% improvement in the accuracy of the end-to-end cognitive load detection process of the XR display system 700 relative to a cognitive load model without PKLR correction.

In some examples, the pupillary light reflex model 720 is trained during use to adapt its predictions to a specific user. In some examples, pupil size can be measured during times of varying cognitive load and luminance over time. These measurements of pupil size, as cognitive load and luminance change, can provide ground truth training data for improving the accuracy of the pupillary light reflex model 720. Thus, the pupillary light reflex model 720 can be trained to predict a user-specific PLR using training data that includes the pupil size data, the local luminance data, and the global luminance data generated while the user uses the XR display system 700. The residual pupil size following luminance correction is then leveraged by the cognitive load model to robustly predict cognitive load.

Figure 18:
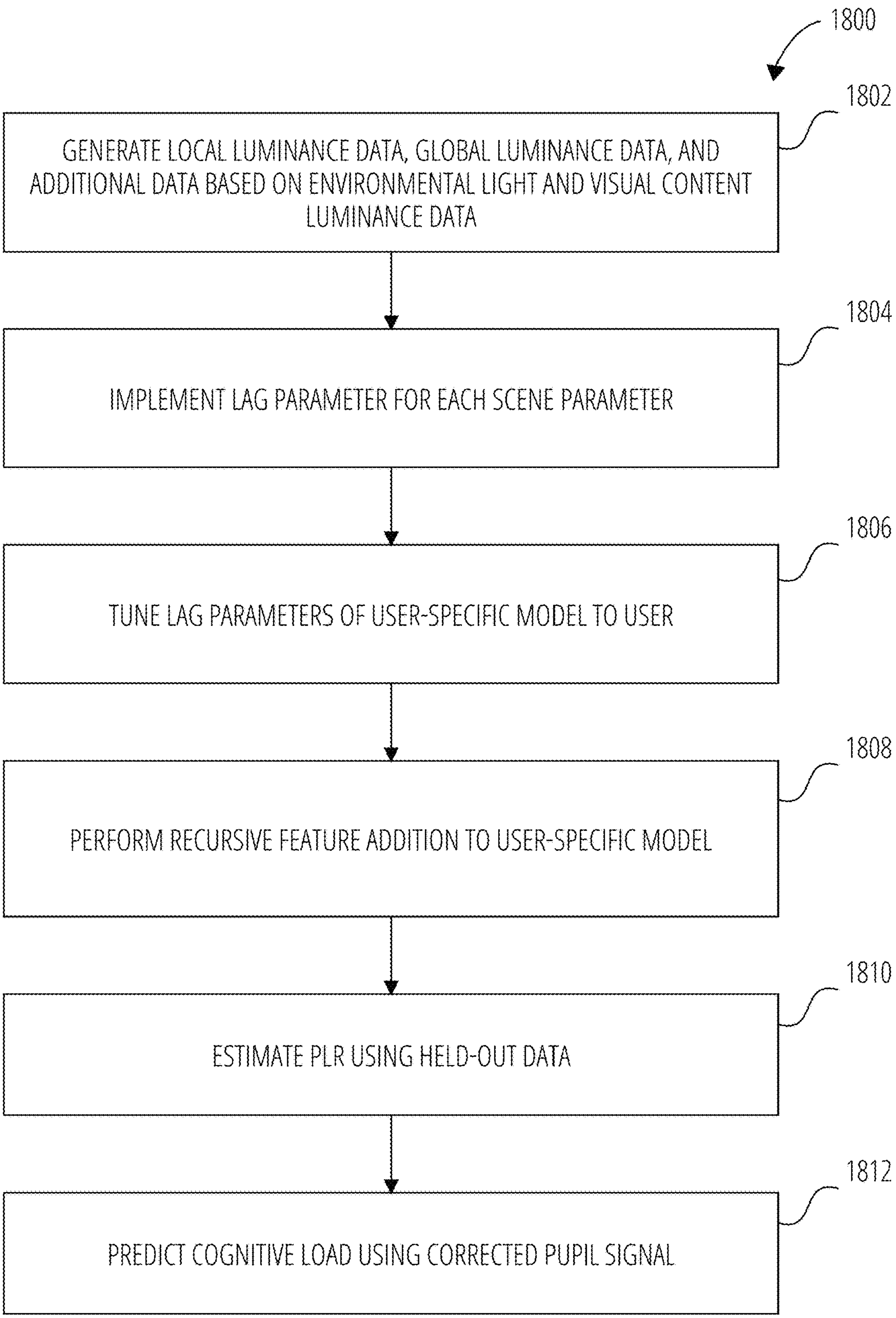
FIG. 18 illustrates a method for further user-specific training of a pupillary light reflex model, in accordance with some examples.

FIG. 18 illustrates a method 1800 for further user-specific training of a pupillary light reflex model. In some examples, a user-specific pupillary light reflex model is trained using random forest regression by recursively adding scene parameters until a trained or optimized user-specific model is provided in which those scene parameters with predictive powers are included and other parameters are excluded or given low weights in the prediction process.

Although the example method 1800 depicts a particular sequence of operations, the sequence may be altered without departing from the scope of the present disclosure. For example, some of the operations depicted may be performed in parallel or in a different sequence that does not materially affect the function of the method 1800. In other examples, different components of an example device or system that implements the method 1800 may perform functions at substantially the same time or in a specific sequence.

According to some examples, the method 1800 includes generating the local luminance data, the global luminance data, and optionally the additional data based on environmental light and visual content luminance data at operation 1802. The local luminance data and global luminance data can be generated according to operation 810 as described above with reference to FIG. 9. The additional data can include one or more of the additional parameters, computed as described above.

According to some examples, the method 1800 includes implementing a respective lag parameter for each scene parameter at operation 1804. In some examples, the scene parameters include the eleven parameters described above, and may also include one or more further parameters (such as local and/or global temporal contrast and/or spatial frequency parameters). The training method 1800 can optimize the performance of the pupillary light reflex model 720 by determining which parameters to use for pupil size prediction for a given user, and/or how much weight to give to each parameter for a given user, as described below.

According to some examples, the method 1800 includes tuning the lag parameters of a user-specific model to predict the specific user's pupil behavior at operation 1806. In some examples, the lag hyperparameter tuning operation 1806 for a given user uses a nested cross-validation approach to optimize the user-specific model's performance in estimating the user's PLR. The outer loop consists of an N-fold (e.g., 4-fold) cross-validation, where the user's data (e.g., pupil size data) is divided into N parts, with N−1 parts used for training and one for testing, repeated N times with different test sets. Within each of these N outer folds, an inner M-fold (e.g., 3-fold) cross-validation is performed on the training data to fine-tune the lag parameter, representing the time delay between visual stimulus (as represented by the scene parameters) and pupillary response. This nested structure allows for robust hyperparameter tuning while maintaining the integrity of the test set, ensuring that the chosen lag parameter values generalize well to unseen data and potentially improves the accuracy of the personalized PLR model for each individual user.

According to some examples, the method 1800 includes performing recursive feature addition to the user-specific model at operation 1808. Following the lag hyperparameter tuning operation 1806, the recursive feature addition operation 1808 is conducted for the user-specific model. In some examples, the same nested cross-validation structure of 4-fold CV with an inner 3-fold CV is used for operation 1808. This process systematically evaluates the importance of each feature (e.g., each scene parameter) by iteratively adding them to the model and assessing their impact on performance. The nested cross-validation approach ensures that feature selection is performed robustly, minimizing the risk of overfitting and producing a personalized set of features that best predict the pupillary light reflex (PLR) for the individual user. By tailoring the feature set to the user, this process aims to optimize the model's ability to learn and adapt to an individual's PLR over time, potentially leading to more accurate PLR correction and thereby more accurate load prediction.

According to some examples, the method 1800 includes estimating PLR using held-out data at operation 1810. In some examples, the user-specific model estimates the pupillary light reflex (PLR) on the held-out data for each fold of the 4-fold cross-validation. Operation 1810 applies the optimized model, with tuned lag parameters and selected scene parameters, to predict the PLR on the unseen test data within each fold. By estimating the PLR on held-out data, the model's generalization ability can be tested, and its performance can be validated in predicting pupillary responses for new, unseen scenarios. Operation 1810 helps ensure that the user-specific model can effectively learn and adapt to an individual's PLR patterns over time, potentially leading to more accurate cognitive load predictions in real-world applications.

According to some examples, the method 1600 includes predicting cognitive load for the held-out user or users using the corrected pupil signal at operation 1812. This operation allows the accuracy of the end-to-end PLR-corrected cognitive load detection process to be evaluated for validation against the ultimate goal of cognitive load prediction (or prediction of another task-evoked pupillary response, such as frustration or engagement as described above).

Once the user-specific model has been trained using method 1800, it can be deployed as the pupillary light reflex model 720 to perform operation 1002 as described above with reference to FIG. 10. In experimental testing, a user-specific model trained according to method 1800 on 30 minutes of user data has been shown to exhibit a more than 9% improvement in the accuracy of the end-to-end cognitive load detection process relative to a cognitive load model without PLR correction. It will be appreciated that longer training periods may yield greater improvements in performance.

In some examples, multiple different model types are used in conjunction. For example, a given XR display system 700 can include one or more of: a group model using two luminance parameters, a group model using 11 parameters, a user-specific model, and a calibrated model. Two or more of these models can be used to predict PLR, and their predictions can be averaged using an averaging function or otherwise aggregated in order to provide PLR correction to the cognitive load model.

In some cases, individual cognitive differences may yield different predictive results. For example, in experimental testing, most of the inaccurate predictions of the model were confined to a subset of users that deviated from the norm. Thus, the system may be capable of capturing and identifying cognitive differences among individuals, such as differences in working memory, motivation, and other traits. In some cases, the predictions of the cognitive load model, corrected for PLR, can be used to measure temporary psychological or cognitive states other than cognitive load per se; for example, the prediction of cognitive load may in some cases indicate a TEPR (task evoked pupillary response), such as engagement or frustration instead of cognitive load, and in some examples the model could be repurposed to predict a user's degree of frustration or engagement with a task, enabling adaptive user interaction that attempts to address or mitigate the user's frustration, increase a user's engagement, and/or otherwise change the operation of the system in response to the user's level of engagement or frustration. It will be appreciated that there may be other applications of the PLR-corrected cognitive load model.

CONCLUSION

Examples described herein may address one or more technical problems associated with XR and cognitive load detection by providing systems, methods, and computer-readable media for cognitive load detection of a user of an XR display system, and dynamic adaptation of interactive software applications of the XR display system to a user's cognitive load, as described above.

Example 1 is an extended reality (XR) display system, comprising: at least one processor; and a memory storing instructions that, when executed by the at least one processor, configure the XR display system to perform operations comprising: causing visual content to be presented to a user's eye by a display device; obtaining pupil size data representative of a pupil size of the user's eye; obtaining gaze vector data representative of a direction of a gaze vector of the user's eye; obtaining environmental light data representative of environmental light propagating toward the user's eye; generating visual content luminance data representative of a luminance of the visual content as presented by the display device; processing the gaze vector data, the visual content luminance data, and the environmental light data to generate: local luminance data representative of a local luminance at a fixation target of the gaze vector; and global luminance data representative of a global luminance of at least a portion of a field of view of the user's eye outside of the fixation target; and processing the pupil size data, the local luminance data, and the global luminance data to generate cognitive load data representative of an inferred cognitive load of the user.

In Example 2, the subject matter of Example 1 includes, the display device, configured to present the visual content to the user's eye; an eye tracking subsystem configured to generate the pupil size data and the gaze vector data; and at least one optical sensor configured to generate the environmental light data; wherein: the obtaining of the pupil size data, gaze vector data, and the environmental light data comprises: generating the pupil size data and gaze vector data by the eye tracking subsystem, and generating the environmental light data by the at least one optical sensor, during the presentation of the visual content.

In Example 3, the subject matter of Example 2 includes, wherein: the presentation of the visual content comprises: processing visual content data representative of the visual content to control the presentation of the visual content to the user's eye by the display device; and the generation of the visual content luminance data comprises: processing the visual content data to generate the visual content luminance data.

In Example 4, the subject matter of Examples 2-3 includes, wherein: the at least one optical sensor comprises an optical sensor configured to: view the visual content as presented by the display device; and generate the visual content luminance data based on the viewed visual content.

In Example 5, the subject matter of Examples 1-4 includes, wherein the operations further comprise: adjusting the visual content based on the inferred cognitive load.

In Example 6, the subject matter of Example 5 includes, wherein: the visual content data is generated by an interactive software application executed by the at least one processor; and the adjusting of the visual content comprises: adjusting a cognitive challenge level of the interactive software application based on the inferred cognitive load; and adjusting the visual content based on the adjusted cognitive challenge level of the interactive software application.

In Example 7, the subject matter of Examples 1-6 includes, wherein: the processing of the gaze vector data, the visual content luminance data, and the environmental light data to generate the local luminance data comprises: processing the gaze vector data to determine a fixation target on the display device toward which the gaze vector is directed; processing the visual content luminance data to determine a luminance of the visual content at the fixation target; processing the environmental light data to determine a luminance of the environmental light at the fixation target; and generating the local luminance data based on the luminance of the visual content at the fixation target and the luminance of the environmental light at the fixation target; and the processing of the gaze vector data, the visual content luminance data, and the environmental light data to generate the global luminance data comprises: processing the visual content luminance data to determine a luminance of the visual content across the field of view; processing the environmental light data to determine a luminance of the environmental light across the field of view; and generating the global luminance data based on the luminance of the visual content across the field of view and the luminance of the environmental light across the field of view.

In Example 8, the subject matter of Example 7 includes, wherein: the processing of the pupil size data, the local luminance data, and the global luminance data to generate the cognitive load data comprises: processing the local luminance data and the global luminance data to generate a predicted pupil size; computing a residual pupil size based on a difference between: the predicted pupil size; and the pupil size indicated by the pupil size data; and applying a cognitive load model to the residual pupil size to generate the cognitive load data.

In Example 9, the subject matter of Example 8 includes, wherein: the cognitive load model comprises a logistic regression model trained using logistic regression of residual pupil size on a known cognitive load of a set of training data samples.

In Example 10, the subject matter of Examples 8-9 includes, wherein the operations further comprise: prior to presenting the visual content, obtaining user baseline pupil size data, the user baseline pupil size data being representative of a baseline pupil size of the user's eye.

In Example 11, the subject matter of Example 10 includes, wherein: the operations further comprise, prior to presenting the visual content: presenting a calibration stimulus to the user's eye by the display device; obtaining calibration pupil size data representative of the pupil size of the user's eye; and processing the calibration pupil size data to generate user pupillary light reflex data, the user pupillary light reflex data being representative of the pupillary light reflex of the user's eye in response to the calibration stimulus; and the predicted pupil size is generated by processing the local luminance data, the global luminance data, the user baseline pupil size data, and the user pupillary light reflex data.

In Example 12, the subject matter of Example 11 includes, wherein: the user pupillary light reflex data comprises an estimated change in pupil size associated with a change in luminance of the calibration stimulus, delayed by a lag parameter.

In Example 13, the subject matter of Example 12 includes, wherein: the lag parameter is between 400 and 600 milliseconds.

In Example 14, the subject matter of Examples 10-13 includes, wherein: the processing of the local luminance data and the global luminance data to generate the predicted pupil size comprises: applying a pupillary light reflex model to the local luminance data and the global luminance data to generate the predicted pupil size, the predicted pupil size being scaled based on the baseline pupil size.

In Example 15, the subject matter of Example 14 includes, wherein: the operations further comprise: training the pupillary light reflex model to predict a user-specific pupillary light reflex using training data comprising the pupil size data, the local luminance data, and the global luminance data generated while the user uses the XR display system.

In Example 16, the subject matter of Examples 14-15 includes, wherein: the local luminance data comprises: a first predictor corresponding to the luminance of the visual content at the fixation target; and a second predictor corresponding to the luminance of the environmental light at the fixation target; the global luminance data comprises: a first predictor corresponding to the luminance of the visual content across the field of view; and a second predictor corresponding to the luminance of the environmental light across the field of view; and the pupillary light reflex model is a random forest regression model trained using random forest regression of the first predictor and second predictor of the local luminance data and the first predictor and second predictor of the global luminance data on a known pupil size of a set of training data samples.

In Example 17, the subject matter of Examples 1-16 includes, wherein: the operations further comprise: processing the gaze vector data, the visual content luminance data, and the environmental light data to generate additional data representative of one or more of the following additional parameters: a local root mean square (RMS) contrast parameter representative of a variation of luminance in a region of the user's field of view where the user's gaze is directed; a global RMS contrast parameter representative of a variation of luminance across the user's field of view; a local Michelson contrast parameter representative of a difference between a highest and a lowest value of luminance in a region of the user's field of view where the user's gaze is directed; a global Michelson contrast parameter representative of a difference between a highest and a lowest value of luminance across the user's field of view; a target-to-local Weber contrast parameter representative of a difference in luminance between a target of the user's gaze and a region of the user's field of view surrounding the target of the user's gaze; a local-to-global Weber contrast parameter representative of a difference in luminance between a region of the user's field of view surrounding a target of the user's gaze and the user's entire field of view; a global blue parameter representative of an amount of blue light in the user's field of view; a global green parameter representative of an amount of green light in the user's field of view; or a global red parameter representative of an amount of red light in the user's field of view; and the cognitive load data is generated by processing the pupil size data, the local luminance data, the global luminance data, and the additional data.

In Example 18, the subject matter of Example 17 includes, wherein: the additional data further comprises, for each of the additional parameters in the additional data, a respective lag parameter representative of an estimated time delay between a change in the additional parameter and a corresponding change in pupil size.

Example 19 is a method for inferring a cognitive load of a user of an extended reality (XR) display system, comprising: presenting visual content to a user's eye from a display device; generating visual content luminance data representative of a luminance of the visual content as presented by the display device; generating, by at least one optical sensor, environmental light data representative of environmental light propagating toward the user's eye; generating, by an eye tracking subsystem, during the presentation of the visual content: pupil size data representative of a pupil size of the user's eye; and gaze vector data representative of a direction of a gaze vector of the user's eye; processing the gaze vector data, the visual content luminance data, and the environmental light data to generate: local luminance data representative of a local luminance at a fixation target of the gaze vector; and global luminance data representative of a global luminance of at least a portion of a field of view of the user's eye outside of the fixation target; and processing the pupil size data, the local luminance data, and the global luminance data to generate cognitive load data representative of an inferred cognitive load of the user.

Example 20 is a non-transitory computer-readable storage medium, the computer-readable storage medium including instructions that when executed by at least one processor of an extended reality (XR) display system, cause the XR display system to perform operations comprising: presenting visual content to a user's eye from a display device; generating visual content luminance data representative of a luminance of the visual content as presented by the display device; generating, by at least one optical sensor, environmental light data representative of environmental light propagating toward the user's eye; generating, by an eye tracking subsystem, during the presentation of the visual content: pupil size data representative of a pupil size of the user's eye; and gaze vector data representative of a direction of a gaze vector of the user's eye; processing the gaze vector data, the visual content luminance data, and the environmental light data to generate: local luminance data representative of a local luminance at a fixation target of the gaze vector; and global luminance data representative of a global luminance of at least a portion of a field of view of the user's eye outside of the fixation target; and processing the pupil size data, the local luminance data, and the global luminance data to generate cognitive load data representative of an inferred cognitive load of the user.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

Other technical features may be readily apparent to one skilled in the art from the following figures, descriptions, and claims.

Glossary

"Extended reality" (XR) refers, for example, to an interactive experience of a real-world environment where physical objects that reside in the real-world are "augmented" or enhanced by computer-generated digital content (also referred to as virtual content or synthetic content). XR can also refer to a system that enables a combination of real and virtual worlds, real-time interaction, and 3D registration of virtual and real objects. A user of an XR system perceives virtual content that appears to be attached to, or interacts with, a real-world physical object.

"Client device" refers, for example, to any machine that interfaces to a communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network.

"Communication network" refers, for example, to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network, and the coupling may be a Code Division Multiple Access (CDMA) connection, a Global System for Mobile communications (GSM) connection, or other types of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth-generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long-range protocols, or other data transfer technology.

"Component" refers, for example, to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various examples, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application-specific integrated circuit (ASIC). A hardware component may also include programmable logic or circuitry that is temporarily configured by software to perform certain operations. For example, a hardware component may include software executed by a general-purpose processor or other programmable processors. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software), may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering examples in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In examples in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some examples, the processors or processor-implemented components may be located in a single geographic location (e.g., within a home environment, an office environment, or a server farm). In other examples, the processors or processor-implemented components may be distributed across a number of geographic locations.

"Computer-readable storage medium" refers, for example, to both machine-storage media and transmission media. Thus, the terms include both storage devices/media and carrier waves/modulated data signals. The terms "machine-readable medium," "computer-readable medium" and "device-readable medium" mean the same thing and may be used interchangeably in this disclosure.

"Machine storage medium" refers, for example, to a single or multiple storage devices and media (e.g., a centralized or distributed database, and associated caches and servers) that store executable instructions, routines and data. The term shall accordingly be taken to include, but not be limited to, solid-state memories, and optical and magnetic media, including memory internal or external to processors. Specific examples of machine-storage media, computer-storage media and device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks The terms "machine-storage medium," "device-storage medium," "computer-storage medium" mean the same thing and may be used interchangeably in this disclosure. The terms "machine-storage media," "computer-storage media," and "device-storage media" specifically exclude carrier waves, modulated data signals, and other such media, at least some of which are covered under the term "signal medium."

"Non-transitory computer-readable storage medium" refers, for example, to a tangible medium that is capable of storing, encoding, or carrying the instructions for execution by a machine.

"Signal medium" refers, for example, to any intangible medium that is capable of storing, encoding, or carrying the instructions for execution by a machine and includes digital or analog communications signals or other intangible media to facilitate communication of software or data. The term "signal medium" shall be taken to include any form of a modulated data signal, carrier wave, and so forth. The term "modulated data signal" means a signal that has one or more of its characteristics set or changed in such a matter as to encode information in the signal. The terms "transmission medium" and "signal medium" mean the same thing and may be used interchangeably in this disclosure.

"User device" refers, for example, to a device accessed, controlled or owned by a user and with which the user interacts perform an action, or an interaction with other users or computer systems.

What is claimed is:

1. An extended reality (XR) display system, comprising:

at least one processor; and a memory storing instructions that, when executed by the at least one processor, configure the XR display system to perform operations comprising:

causing visual content to be presented to a user's eye by a display device;

obtaining pupil size data representative of a pupil size of the user's eye;

obtaining gaze vector data representative of a direction of a gaze vector of the user's eye;

obtaining environmental light data representative of environmental light propagating toward the user's eye;

generating visual content luminance data representative of a luminance of the visual content as presented by the display device;

processing the gaze vector data, the visual content luminance data, and the environmental light data to generate:

local luminance data representative of a local luminance at a fixation target of the gaze vector; and global luminance data representative of a global luminance of at least a portion of a field of view of the user's eye outside of the fixation target; and processing the pupil size data, the local luminance data, and the global luminance data to generate cognitive load data representative of an inferred cognitive load of the user.

2. The XR display system of claim 1, further comprising:
the display device, configured to present the visual content to the user's eye;
an eye tracking subsystem configured to generate the pupil size data and the gaze vector data; and
at least one optical sensor configured to generate the environmental light data;
wherein:
the obtaining of the pupil size data, gaze vector data, and the environmental light data comprises:
generating the pupil size data and gaze vector data by the eye tracking subsystem, and generating the environmental light data by the at least one optical sensor, during the presentation of the visual content.

3. The XR display system of claim 2, wherein:
the presentation of the visual content comprises:
processing visual content data representative of the visual content to control the presentation of the visual content to the user's eye by the display device; and
the generation of the visual content luminance data comprises:
processing the visual content data to generate the visual content luminance data.

4. The XR display system of claim 2, wherein:
the at least one optical sensor comprises an optical sensor configured to:
view the visual content as presented by the display device; and
generate the visual content luminance data based on the viewed visual content.

5. The XR display system of claim 1, wherein the operations further comprise:
adjusting the visual content based on the inferred cognitive load.

6. The XR display system of claim 5, wherein:
the visual content data is generated by an interactive software application executed by the at least one processor; and
the adjusting of the visual content comprises:
adjusting a cognitive challenge level of the interactive software application based on the inferred cognitive load; and
adjusting the visual content based on the adjusted cognitive challenge level of the interactive software application.

7. The XR display system of claim 1, wherein:
the processing of the gaze vector data, the visual content luminance data, and the environmental light data to generate the local luminance data comprises:
processing the gaze vector data to determine a fixation target on the display device toward which the gaze vector is directed;
processing the visual content luminance data to determine a luminance of the visual content at the fixation target;
processing the environmental light data to determine a luminance of the environmental light at the fixation target; and
generating the local luminance data based on the luminance of the visual content at the fixation target and the luminance of the environmental light at the fixation target; and
the processing of the gaze vector data, the visual content luminance data, and the environmental light data to generate the global luminance data comprises:
processing the visual content luminance data to determine a luminance of the visual content across the field of view;
processing the environmental light data to determine a luminance of the environmental light across the field of view; and
generating the global luminance data based on the luminance of the visual content across the field of view and the luminance of the environmental light across the field of view.

8. The XR display system of claim 7, wherein:
the processing of the pupil size data, the local luminance data, and the global luminance data to generate the cognitive load data comprises:
processing the local luminance data and the global luminance data to generate a predicted pupil size;
computing a residual pupil size based on a difference between:
the predicted pupil size; and
the pupil size indicated by the pupil size data; and
applying a cognitive load model to the residual pupil size to generate the cognitive load data.

9. The XR display system of claim 8, wherein:
the cognitive load model comprises a logistic regression model trained using logistic regression of residual pupil size on a known cognitive load of a set of training data samples.

10. The XR display system of claim 8, wherein the operations further comprise:
prior to presenting the visual content, obtaining user baseline pupil size data, the user baseline pupil size data being representative of a baseline pupil size of the user's eye.

11. The XR display system of claim 10, wherein:
the operations further comprise, prior to presenting the visual content:
presenting a calibration stimulus to the user's eye by the display device;
obtaining calibration pupil size data representative of the pupil size of the user's eye; and
processing the calibration pupil size data to generate user pupillary light reflex data, the user pupillary light reflex data being representative of the pupillary light reflex of the user's eye in response to the calibration stimulus; and
the predicted pupil size is generated by processing the local luminance data, the global luminance data, the user baseline pupil size data, and the user pupillary light reflex data.

12. The XR display system of claim 11, wherein:
the user pupillary light reflex data comprises an estimated change in pupil size associated with a change in luminance of the calibration stimulus, delayed by a lag parameter.

13. The XR display system of claim 12, wherein:
the lag parameter is between 400 and 600 milliseconds.

14. The XR display system of claim 10, wherein:
the processing of the local luminance data and the global luminance data to generate the predicted pupil size comprises:
applying a pupillary light reflex model to the local luminance data and the global luminance data to generate the predicted pupil size, the predicted pupil size being scaled based on the baseline pupil size.

15. The XR display system of claim 14, wherein:
the operations further comprise:
training the pupillary light reflex model to predict a user-specific pupillary light reflex using training data comprising at least the pupil size data, the local luminance data, and the global luminance data generated while the user uses the XR display system.

16. The XR display system of claim 14, wherein:
the local luminance data comprises:
a first predictor corresponding to the luminance of the visual content at the fixation target; and
a second predictor corresponding to the luminance of the environmental light at the fixation target;
the global luminance data comprises:
a first predictor corresponding to the luminance of the visual content across the field of view; and
a second predictor corresponding to the luminance of the environmental light across the field of view; and
the pupillary light reflex model is a random forest regression model trained using random forest regression of the first predictor and second predictor of the local luminance data and the first predictor and second predictor of the global luminance data on a known pupil size of a set of training data samples.

17. The XR display system of claim 1, wherein:
the operations further comprise:
processing the gaze vector data, the visual content luminance data, and the environmental light data to generate additional data representative of one or more of the following additional parameters:
a local root mean square (RMS) contrast parameter representative of a variation of luminance in a region of the user's field of view where the user's gaze is directed;
a global RMS contrast parameter representative of a variation of luminance across the user's field of view;
a local Michelson contrast parameter representative of a difference between a highest and a lowest value of luminance in a region of the user's field of view where the user's gaze is directed;
a global Michelson contrast parameter representative of a difference between a highest and a lowest value of luminance across the user's field of view;
a target-to-local Weber contrast parameter representative of a difference in luminance between a target of the user's gaze and a region of the user's field of view surrounding the target of the user's gaze;
a local-to-global Weber contrast parameter representative of a difference in luminance between a region of the user's field of view surrounding a target of the user's gaze and the user's entire field of view;
a global blue parameter representative of an amount of blue light in the user's field of view;
a global green parameter representative of an amount of green light in the user's field of view;
a global red parameter representative of an amount of red light in the user's field of view;
a local temporal contrast parameter representative of a temporal change in luminance within the region of the user's field of view where the user's gaze is directed;
a global temporal contrast parameter representative of a temporal change in luminance across the user's field of view;
a local edge density parameter representative of a spatial frequency of spatial changes in luminance across the region of the user's field of view where the user's gaze is directed; or
a global edge density parameter representative of a spatial frequency of spatial changes in luminance across the user's field of view; and
the cognitive load data is generated by processing the pupil size data, the local luminance data, the global luminance data, and the additional data.

18. The XR display system of claim 17, wherein:
the additional data further comprises, for each of the additional parameters in the additional data, a respective lag parameter representative of an estimated time delay between a change in the additional parameter and a corresponding change in pupil size.

19. A method for inferring a cognitive load of a user of an extended reality (XR) display system, comprising:
presenting visual content to a user's eye from a display device;
generating visual content luminance data representative of a luminance of the visual content as presented by the display device;
generating, by at least one optical sensor, environmental light data representative of environmental light propagating toward the user's eye;
generating, by an eye tracking subsystem, during the presentation of the visual content:
pupil size data representative of a pupil size of the user's eye; and
gaze vector data representative of a direction of a gaze vector of the user's eye;
processing the gaze vector data, the visual content luminance data, and the environmental light data to generate:
local luminance data representative of a local luminance at a fixation target of the gaze vector; and
global luminance data representative of a global luminance of at least a portion of a field of view of the user's eye outside of the fixation target; and
processing the pupil size data, the local luminance data, and the global luminance data to generate cognitive load data representative of an inferred cognitive load of the user.

20. A non-transitory computer-readable storage medium, the computer-readable storage medium including instructions that when executed by at least one processor of an extended reality (XR) display system, cause the XR display system to perform operations comprising:
presenting visual content to a user's eye from a display device;
generating visual content luminance data representative of a luminance of the visual content as presented by the display device;
generating, by at least one optical sensor, environmental light data representative of environmental light propagating toward the user's eye;
generating, by an eye tracking subsystem, during the presentation of the visual content:
pupil size data representative of a pupil size of the user's eye; and
gaze vector data representative of a direction of a gaze vector of the user's eye;
processing the gaze vector data, the visual content luminance data, and the environmental light data to generate:

local luminance data representative of a local luminance at a fixation target of the gaze vector; and global luminance data representative of a global luminance of at least a portion of a field of view of the user's eye outside of the fixation target; and processing the pupil size data, the local luminance data, and the global luminance data to generate cognitive load data representative of an inferred cognitive load of the user.

* * * * *